(12) United States Patent
Adney et al.

(10) Patent No.: US 7,393,673 B2
(45) Date of Patent: *Jul. 1, 2008

(54) **THERMAL TOLERANT EXOGLUCANASE FROM *ACIDOTHERMUS CELLULOLYTICUS***

(75) Inventors: William S. Adney, Golden, CO (US); Shi-You Ding, Golden, CO (US); Todd B. Vinzant, Golden, CO (US); Michael E. Himmel, Littleton, CO (US); Stephen R. Decker, Berthoud, CO (US); Suzanne Lantz McCarter, Denver, CO (US)

(73) Assignee: Midwest Research Institute, Kansas City, MO (US)

( * ) Notice: Subject to any disclaimer, the term of this patent is extended or adjusted under 35 U.S.C. 154(b) by 190 days.

This patent is subject to a terminal disclaimer.

(21) Appl. No.: 09/917,384

(22) Filed: Jul. 28, 2001

(65) Prior Publication Data

US 2003/0096342 A1    May 22, 2003

(51) Int. Cl.
| | |
|---|---|
| C12N 9/00 | (2006.01) |
| C12N 9/24 | (2006.01) |
| C12N 9/42 | (2006.01) |
| C12Q 1/68 | (2006.01) |
| C12P 21/06 | (2006.01) |
| C07K 1/00 | (2006.01) |
| C07K 16/00 | (2006.01) |

(52) U.S. Cl. .................. 435/209; 435/200; 435/183; 435/6; 435/69.1; 435/41; 530/350; 530/387.1
(58) Field of Classification Search ................. 435/183, 435/195, 200, 209, 341, 262, 277, 4, 6, 41; 530/350, 387.1
See application file for complete search history.

(56) References Cited

U.S. PATENT DOCUMENTS

| | | | |
|---|---|---|---|
| 5,110,735 A | 5/1992 | Tucker et al. | |
| 5,366,884 A | 11/1994 | Adney et al. | |
| 5,432,075 A | 7/1995 | Himmel et al. | |
| 5,514,584 A | 5/1996 | Lastick et al. | |
| 5,536,655 A | 7/1996 | Thomas et al. | |
| 5,712,142 A | 1/1998 | Adney et al. | |
| 6,013,860 A | 1/2000 | Himmel et al. | |
| 6,126,698 A | 10/2000 | Liu et al. | |

OTHER PUBLICATIONS

Zverlov Vladimer et al., "Properties and gene structure of a bifunctional cellulolytic enzyme (CdlA) from the extreme thermophile 'Anaerocellum thermophilum' with separate glycosyl hydrolase family,"Microbiology, vol. 144, No. 2, Feb. 1998, pp. 457-465, XP002195181.

Shend Hua et al., "Cellobiohyfrolase B, a second exo-cellobiohydrolase from the cellulolytic bacterium *Cellulomonas fimi*." Biochemical Journal, vol. 311, No. 1, 1995, pp. 67-74, XP001064588.

Laymon R.A. et al. Endoglucanase E-1 Precursor (EC 3.2.1.4) (Endo-1, 4-Beta-Glucanase E1) (Cellulase E1) (Endocellulase E1), Swissprot 'Online! Accession P54583, Oct. 1, 1996.—ZP002195183.

Tomme P. et al., Characterization and affinity applications of cellulose-binding domains. Journal of Chromatography B: Biomedical Sciences & Applications, Elsevier Science Publishers, NL, vol. 715, No. 1, pp. 283-296, Sep. 11, 1998. XP004147002.

Jung, E.D. et al., Endoglucanase E-4 Precursor (EC 3.2.1.4) (Endo-1, 4-Beta-Glucanase E-4) (Cellulase E-4) (Cellulase E4), Swissprot 'Online! Accession P26221, May 1, 1992.—XP002195184.

Meinke A. et al., "Endoglucanase B Precursor (EC 3.2.1.4) (Endo-1, 4-Beta-Glucanase B) (Cellulase B)" Swissprot 'Online! Accession P26225, May 1, 1992.—XP002195185.

Al-Sulami, A. A., et al. "Purification and Properties of Cellulases from a Local Isolate of *Cellulomonas flavigena*." Dirasat, vol. 19B, No. 4 (1992), pp. 139-155 (Univ.Jordan).

Baker, J. O., et al. "Synergism Between Purified Bacterial and Fungal Cellulases." *Enzymatic Degradation of Insoluble Carbohydrates*, Am. Chem. Society Symp. Ser. vol. 618 (1995) pp. 113-141.

*Primary Examiner*—Rebecca E. Prouty
*Assistant Examiner*—Iqbal Chowdhury
(74) *Attorney, Agent, or Firm*—Paul J. White; Kenneth Richardson; Mark D. Trenner

(57) ABSTRACT

The invention provides a thermal tolerant cellulase that is a member of the glycoside hydrolase family. The invention further discloses this cellulase as Gux1. Gux1 has been isolated and characterized from *Acidothermus cellulolyticus*. The invention further provides recombinant forms of the identified Gux1. Methods of making and using Gux1 polypeptides, including fusions, variants, and derivatives, are also disclosed.

19 Claims, 2 Drawing Sheets

THERMAL TOLERANT EXOGLUCANASE FROM *ACIDOTHERMUS CELLULOLYTICUS*

GOVERNMENT INTERESTS

The United States Government has rights in this invention under Contract No. DE-AC36-99GO10337 between the United States Department of Energy and the National Renewable Energy Laboratory, a Division of the Midwest Research Institute.

FIELD OF THE INVENTION

The invention generally relates to a novel exoglucanase from *Acidothermus cellulolyticus*, Gux1. More specifically, the invention relates to purified and isolated Gux1 polypeptides, nucleic acid molecules encoding the polypeptides, and processes for production and use of Gux1, as well as variants and derivatives thereof.

BACKGROUND OF THE INVENTION

Plant biomass as a source of energy production can include agricultural and forestry products, associated by-products and waste, municipal solid waste, and industrial waste. In addition, over 50 million acres in the United States are currently available for biomass production, and there are a number of terrestrial and aquatic crops grown solely as a source for biomass (A Wiselogel, et al. Biomass feedstocks resources and composition. In C E Wyman, ed. Handbook on Bioethanol: Production and Utilization. Washington, D.C.: Taylor & Francis, 1996, pp 105-118). Biofuels produced from biomass include ethanol, methanol, biodiesel, and additives for reformulated gasoline. Biofuels are desirable because they add little, if any, net carbon dioxide to the atmosphere and because they greatly reduce ozone formation and carbon monoxide emissions as compared to the environmental output of conventional fuels. (P Bergeron. Environmental impacts of bioethanol. In C E Wyman, ed. Handbook on Bioethanol: Production and Utilization. Washington, D.C.: Taylor & Francis, 1996, pp 90-103).

Plant biomass is the most abundant source of carbohydrate in the world due to the lignocellulosic materials composing the cell walls of all higher plants. Plant cell walls are divided into two sections, the primary and the secondary cell walls. The primary cell wall, which provides structure for expanding cells (and hence changes as the cell grows), is composed of three major polysaccharides and one group of glycoproteins. The predominant polysaccharide, and most abundant source of carbohydrates, is cellulose, while hemicellulose and pectin are also found in abundance. Cellulose is a linear beta-(1,4)-D-glucan and comprises 20% to 30% of the primary cell wall by weight. The secondary cell wall, which is produced after the cell has completed growing, also contains polysaccharides and is strengthened through polymeric lignin covalently cross-linked to hemicellulose.

Carbohydrates, and cellulose in particular can be converted to sugars by well-known methods including acid and enzymatic hydrolysis. Enzymatic hydrolysis of cellulose requires the processing of biomass to reduce size and facilitate subsequent handling. Mild acid treatment is then used to hydrolyze part or all of the hemicellulose content of the feedstock. Finally, cellulose is converted to ethanol through the concerted action of cellulases and saccharolytic fermentation (simultaneous saccharification fermentation (SSF)). The SSF process, using the yeast *Saccharomyces cerevisiae* for example, is often incomplete, as it does not utilize the entire sugar content of the plant biomass, namely the hemicellulose fraction.

The cost of producing ethanol from biomass can be divided into three areas of expenditure: pretreatment costs, fermentation costs, and other costs. Pretreatment costs include biomass milling, pretreatment reagents, equipment maintenance, power and water, and waste neutralization and disposal. The fermentation costs can include enzymes, nutrient supplements, yeast, maintenance and scale-up, and waste disposal. Other costs include biomass purchase, transportation and storage, plant labor, plant utilities, ethanol distillation, and administration (which may include technology-use licenses). One of the major expenses incurred in SSF is the cost of the enzymes, as about one kilogram of cellulase is required to fully digest 50 kilograms of cellulose. Economical production of cellulase is also compounded by factors such as the relatively slow gowth rates of cellulase-producing organisms, levels of cellulase expression, and the tendency of enzyme-dependent processes to partially or completely inactivate enzymes due to conditions such as elevated temperature, acidity, proteolytic degradation, and solvent degradation.

Enzymatic degradation of cellulose requires the coordinate action of at least three different types of cellulases. Such enzymes are given an Enzyme Commission (EC) designation according to the Nomenclature Committee of the International Union of Biochemistry and Molecular Biology (Eur. J. Biochem. 264: 607-609 and 610-650, 1999). Endo-beta-(1,4)-glucanases (EC 3.2.1.4) cleave the cellulose strand randomly along its length, thus generating new chain ends. Exo-beta-(1,4)-glucanases (EC 3.2.1.91) are processive enzymes and cleave cellobiosyl units (beta-(1,4)-glucose dimers) from free ends of cellulose strands. Lastly, beta-D-glucosidases (cellobiases: EC 3.2.1.21) hydrolyze cellobiose to glucose. All three of these general activities are required for efficient and complete hydrolysis of a polymer such as cellulose to a subunit, such as the simple sugar, glucose.

Highly thermostable enzymes have been isolated from the cellulolytic thermophile *Acidothermus cellulolyticus* gen. nov., sp. nov., a bacterium originally isolated from decaying wood in an acidic, thermal pool at Yellowstone National Park. A. Mohagheghi et al., (1986) *Int. J. Systematic Bacteriology*, 36(3): 435-443. One cellulase enzyme produced by this organism, the endoglucanase EI, is known to display maximal activity at 75° C. to 83° C. M.P. Tucker et al. (1989), *Bio/Technology*, 7(8): 817-820. E1 endoglucanase has been described in U.S. Pat. No. 5,275,944. The *A. cellulolyticus* E1 endoglucanase is an active cellulase; in combination with the exocellulase CBH I from *Trichoderma reesei*, E1 gives a high level of saccharification and contributes to a degree of synergism. Baker J O et al. (1994), *Appl. Biochem. Biotechnol.*, 45/46: 245-256. The gene coding EI catalytic and carbohydrate binding domains and linker peptide were described in U.S. Pat. No. 5,536,655. E1 has also been expressed as a stable, active enzyme from a wide variety of hosts, including *E. coli, Streptomyces lividans, Pichia pastoris*, cotton, tobacco, and *Arabidopsis* (Dai Z, Hooker B S, Anderson D B, Thomas S R. Transgenic Res. 2000 February; 9(l):43-54).

There is a need within the art to generate alternative cellulase enzymes capable of assisting in the commercial-scale processing of cellulose to sugar for use in biofuel production. Against this backdrop the present invention has been developed. The potential exists for the successful, commercial-scale expression of heterologous cellulase polypeptides, and in particular novel cellulase polypeptides with or without any one or more desirable properties such as thermal tolerance, and partial or complete resistance to extreme pH inactivation, proteolytic inactivation, solvent inactivation, chaotropic agent inactivation, oxidizing agent inactivation, and detergent inactivation. Such expression can occur in fungi, bacteria, and other hosts.

SUMMARY OF THE INVENTION

The present invention provides Gux1, a novel member of the glycoside hydrolase (GH) family of enzymes, and in particular a thermal tolerant glycoside hydrolase useful in the degradation of cellulose. Gux1 polypeptides of the invention include those having an amino acid sequence shown in SEQ ID NO: 1, as well as polypeptides having substantial amino acid sequence identity to the amino acid sequence of SEQ ID NO: 1 and useful fragments thereof, including, a catalytic domain having significant sequence similarity to the GH48 family, a first carbohydrate binding domain (type II) and a second carbohydrate binding domain (type III).

The invention also provides a polynucleotide molecule encoding Gux1 polypeptides and fragments of Gux1 polypeptides, for example catalytic and carbohydrate binding domains. Polynucleotide molecules of the invention include those molecules having a nucleic acid sequence as shown in SEQ ID NO: 2; those that hybridize to the nucleic acid sequence of SEQ ID NO: 2 under high stringency conditions; and those having substantial nucleic acid identity with the nucleic acid sequence of SEQ ID NO: 2.

The invention includes variants and derivatives of the Gux1 polypeptides, including fusion proteins. For example, fusion proteins of the invention include Gux1 polypeptide fused to a heterologous protein or peptide that confers a desired function. The heterologous protein or peptide can facilitate purification, oligomerization, stabilization, or secretion of the Gux1 polypeptide, for example. As further examples, the heterologous polypeptide can provide enhanced activity, including catalytic or binding activity, for Gux1 polypeptides, where the enhancement is either additive or synergistic. A fusion protein of an embodiment of the invention can be produced, for example, from an expression construct containing a polynucleotide molecule encoding Gux1 polypeptide in frame with a polynucleotide molecule for the heterologous protein. Embodiments of the invention also comprise vectors, plasmids, expression systems, host cells, and the like, containing a Gux1 polynucleotide molecule. Genetic engineering methods for the production of Gux1 polypeptides of embodiments of the invention include expression of a polynucleotide molecule in cell free expression systems and in cellular hosts, according to known methods.

The invention further includes compositions containing a substantially purified Gux1 polypeptide of the invention and a carrier. Such compositions are administered to a biomass containing cellulose for the reduction or degradation of the cellulose.

The invention also provides reagents, compositions, and methods that are useful for analysis of Gux1 activity.

These and various other features as well as advantages which characterize the present invention will be apparent from a reading of the following detailed description and a review of the associated drawings.

The following Tables 4 and 5 includes sequences used in describing embodiments of the present invention. In Table 4, the abbreviations are as follows: CD, catalytic domain; CBD_II, carbohydrate binding domain type II; CBD_III carbohydrate binding domain type III; and FN-III, fibronectin domain type III. When used herein, N* indicates a string of unknown nucleic acid units, and X* indicates a string of unknown amino acid units, for example about 50 or more. Table 4 includes approximate start and stop information for segments, and Table 5 includes amino acid sequence data for segments.

TABLE 4

Nucleotide and polypeptide segments.

| Gux1 Segment | base BEGIN | base END | Length, bp | aa BEGIN No. | aa | aa END No. | aa | Length, aa | SEQ ID No. (amino acid) | SEQ ID No. (nucleotide) |
|---|---|---|---|---|---|---|---|---|---|---|
| Total length | 1 | 3366 | 3366 | 1 | M | 1121 | S | 1121 | 1 | 2 |
| Signal (potential) | 1 | 102 | 102 | 1 | M | 34 | A | 34 | 3 | |
| CBD III | 103 | 561 | 459 | 35 | A | 187 | A | 153 | 4 | |
| CD (GH48) | 691 | 2610 | 1920 | 231 | N | 870 | P | 640 | 5 | |
| FN-III | 2701 | 2955 | 255 | 901 | D | 985 | G | 85 | 6 | |
| CBD II | 3061 | 3363 | 303 | 1021 | G | 1121 | S | 101 | 7 | |

TABLE 5

Gene/polypeptide segments with amino acid sequences.

| SEQ ID No. (amino acid) | SEQ ID No. (nucleotide) | Gux1 Segment | segment data |
|---|---|---|---|
| 1 | 2 | Total length | SEQ ID NO: 1 (see Table 1); SEQ ID NO: 2 (see Table 2) |
| 3 | | Signal (potential) | MPGLRRRLRAGIVAAAALGSLVSGLVAVAPVAHA |
| 4 | | CBD_III | AVTLKAQYKNNDSAPSDNQIKPGLQLVNTGSSSVDLSTVTVRYWFTRDGGSSTLVYNCDWAA MGCGNIRASFGSVNPATPTADTYLQLSFTGGTLAAGGSTGEIQNRVNKSDWSNFDETNDYSY GTNTTFQDWTKVTVYVNGVLVWGTEPSGA |
| 5 | | CD (GH48) | NDPYIQRFLTMYNKIHDPANGYFSPQGIPYHSVETLIVEAPDYGHETTSEAYSFWLWLEATY GAVTGNWTPFNNAWTTMETYMIPQHADQPNNASYNPNSPASYAPEEPLPSMYPVAIDSSVPV |

TABLE 5-continued

Gene/polypeptide segments with amino acid sequences.

| SEQ ID No. (amino acid) | SEQ ID No. (nucleotide) Segment | Gux1 segment data |
|---|---|---|
|  |  | GHDPLAAELQSTYGTPDIYGMHWLADVDNIYGYGDSPGGGCELGPSAKGVSYINTFQRGSQE<br>SVWETVTQPTCDNGKYGGAHGYVDLFIQGSTPPQWKYTDAPDADARAVQAAYWAYTWASAQG<br>KASAIAPTIAKASQTGDYLRYSLFDKYFKQVGNCYPASSCPGATGRQSETYLIGWYYAWGGS<br>SQGWAWRIGDGAAHFGYQNPLAAWAMSNVTPLIPLSPTAKSDWAASLQRQLEFYQWLQSAEG<br>AIAGGATNSWNGNYGTPPAGDSTFYGMAYDWEPVYHDPPSNNWFGFQAWSMERVAEYYVTG<br>DPKAKALLDKWVAWVKPNVTTGASWSIPSNLSWSGQPDTWNPSNPGTNANLHVTITSSGQDV<br>GVAAALAKTLEYYAAKSGDTASRDLAKGLLDSMWNNDQDSLGVSTPETRTDYSRFTQVYDPT<br>TGDGLYIPSGWTGTMPNGDQIKPGATFLSIRSWYTKDPQWSKVQAYLNGGPAPTFNYHRFWA<br>ESDFAMANADFGMLFPSGS<u>P</u> |
| 6 | FN-III | <u>D</u>TTPPSVPTGLQVTGTTTSSVSLSWTASTDNVGVAHYNVYRNGTLVGQPTATSFTDTGLAAG<u>T</u>SYTYTVAAVDAAGNTSAQSFA<u>G</u> |
| 7 | CBD II | <u>G</u>ASCTATYVVNSDWGSGFTTTVTVTNTGTRATSGWTVTWSFAGNQTVTNYWNTAL<u>T</u>OSGKSVTAKNLSYNNVIQPGQSTTFGFNGSYSGTNTAPTLSCTA<u>S</u> |

DETAILED DESCRIPTION

Definitions

Figure 1:
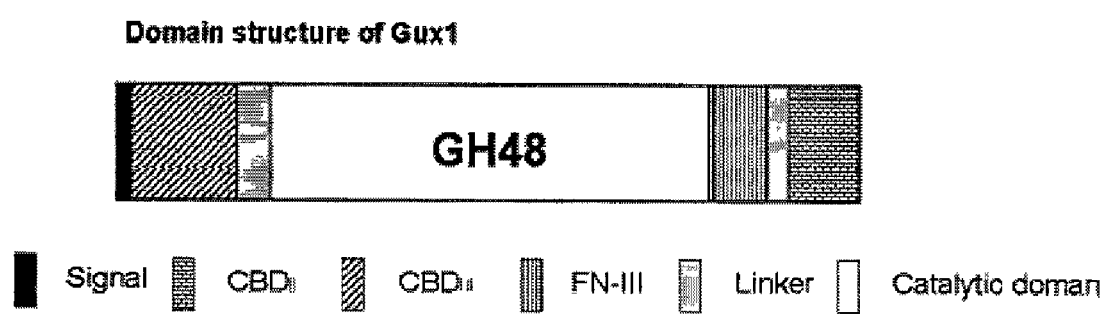
FIG. 1 is a schematic representation of the gene sequence and amino acid segment organization.

The following definitions are provided to facilitate understanding of certain terms used frequently herein and are not meant to limit the scope of the present disclosure:

"Amino acid" refers to any of the twenty naturally occuring amino acids as well as any modified amino acid sequences. Modifications may include natural processes such as post-translational processing, or may include chemical modifications which are known in the art. Modifications include but are not limited to: phosphorylation, ubiquitination, acetylation, amidation, glycosylation, covalent attachment of flavin, ADP-ribosylation, cross linking, iodination, methylation, and alike.

"Antibody" refers to a Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other well known recombinant antibodies are included in the present invention.

"Antisense" refers to polynucleotide sequences that are complementary to target "sense" polynucleotide sequence.

"Binding activity" refers to any activity that can be assayed by characterizing the ability of a polypeptide to bind to a substrate. The substrate can be a polymer such as cellulose or can be a complex molecule or aggregate of molecules where the entire moiety comprises at least some cellulose.

"Cellulase activity" refers to any activity that can be assayed by characterizing the enzymatic activity of a cellulase. For example, cellulase activity can be assayed by determining how much reducing sugar is produced during a fixed amount of time for a set amount of enzyme (see Irwin et al., (1998) *J. Bacteriology*, 1709-1714). Other assays are well known in the art and can be substituted.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

"Expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., 1989, *Molecular cloning: A Laboratory Manual*, 18.1-18.88).

"Fusion protein" refers to a first protein having attached a second, heterologous protein. Preferably, the heterologous protein is fused via recombinant DNA techniques, such that the first and second proteins are expressed in frame. The heterologous protein can confer a desired characteristic to the fusion protein, for example, a detection signal, enhanced stability or stabilization of the protein, facilitated oligomerization of the protein, or facilitated purification of the fusion protein. Examples of heterologous proteins useful in the fusion proteins of the invention include molecules having one or more catalytic domains of Gux1, one or more binding domains of Gux1, one or more catalytic domains of a glycoside hydrolase other than Gux1, one or more binding domains of a glycoside hydrolase other than Gux1, or any combination thereof. Further examples include immunoglobulin molecules and portions thereof, peptide tags such as histidine tag (6-His) (SEQ ID NO: 8), leucine zipper, substrate targeting moieties, signal peptides, and the like. Fusion proteins are also meant to encompass variants and derivatives of Gux1 polypeptides that are generated by conventional site-directed mutagenesis and more modern techniques such as directed evolution, discussed infra.

"Genetically engineered" refers to any recombinant DNA or RNA method used to create a prokaryotic or eukaryotic host cell that expresses a protein at elevated levels, at lowered levels, or in a mutated form. In other words, the host cell has been transfected, transformed, or transduced with a recombinant polynucleotide molecule, and thereby been altered so as to cause the cell to alter expression of the desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetically engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, *Proc Natl Acad Sci USA* 96(6):2758-63).

"Glycoside hydrolase family" refers to a family of enzymes which hydrolyze the glycosidic bond between two or more carbohydrates or between a carbohydrate and a non-carbohydrate moiety (Henrissat B., (1991) Biochem. J., 280: 309-316). Identification of a putative glycoside hydrolase family member is made based on an amino acid sequence comparison and the finding of significant sequence similarity within the putative member's catalytic domain, as compared to the catalytic domains of known family members.

"Homology" refers to a degree of complementarity between polynucleotides, having significant effect on the efficiency and strength of hybridization between polynucleotide molecules. The term also can refer to a degree of similarity between polypeptides. Two polypeptides having greater than or equal to about 60% similarity are presumptively homologous.

"Host cell" or "host cells" refers to cells expressing a heterologous polynucleotide molecule. Host cells of the present invention express polynucleotides encoding Gux1 or a fragment thereof. Examples of suitable host cells useful in the present invention include, but are not limited to, prokaryotic and eukaryotic cells. Specific examples of such cells include bacteria of the genera *Escherichia, Bacillus*, and *Salmonella*, as well as members of the genera *Pseudomonas, Streptomyces*, and *Staphylococcus*; fungi, particularly filamentous fungi such as *Trichoderma* and *Aspergillus, Phanerochaete chrysosporium* and other white rot fungi; also other fungi including *Fusaria*, molds, and yeast including *Saccharomyces* sp., *Pichia* sp., and *Candida* sp. and the like; plants e.g. *Arabidopsis*, cotton, barley, tobacco, potato, and aquatic plants and the like; SF9 insect cells (Summers and Smith, 1987, *Texas Agriculture Experiment Station Bulletin*, 1555), and the like. Other specific examples include mammalian cells such as human embyonic kidney cells (293 cells), Chinese hamster ovary (CHO) cells (Puck et al., 1958, *Proc. Natl. Acad. Sci. USA* 60, 1275-1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213), murine myeloma cells such as P3/NSI/1-Ag4-1 (ATCC TIB-18), P3X63Ag8 (ATCC TIB-9), SP2/0-Ag14 (ATCC CRL-1581) and the like.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

"Identity" refers to a comparison between pairs of nucleic acid or amino acid molecules. Methods for determining sequence identity are known. See, for example, computer programs commonly employed for this purpose, such as the Gap program (Wisconsin Sequence Analysis Package, Version 8 for Unix, Genetics Computer Group, University Research Park, Madison Wis.), that uses the algorithm of Smith and Waterman, 1981, *Adv. Appl. Math.*, 2: 482-489.

"Isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature.

"Nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

"Polynucleotide" refers to a linear sequence of nucleotides. The nucleotides may be ribonucleotides, or deoxyribonucleotides, or a mixture of both. Examples of polynucleotides in the context of the present invention include single and double stranded DNA, single and double stranded RNA, and hybrid molecules having mixtures of single and double stranded DNA and RNA. The polynucleotides of the present invention may contain one or more modified nucleotides.

"Protein," "peptide," and "polypeptide" are used interchangeably to denote an amino acid polymer or a set of two or more interacting or bound amino acid polymers.

"Purify," or "purified" refers to a target protein that is free from at least 5-10% of contaminating proteins. Purification of a protein from contaminating proteins can be accomplished using known techniques, including ammonium sulfate or ethanol precipitation, acid precipitation, heat precipitation, anion or cation exchange chromatography, phosphocellulose chromatography, hydrophobic interaction chromatography, affinity chromatography, hydroxylapatite chromatography, size-exclusion chromatography, and lectin chromatography. Various protein purification techniques are illustrated in *Current Protocols in Molecular Biology*, Ausubel et al., eds. (Wiley & Sons, New York, 1988, and quarterly updates).

"Selectable marker" refers to a marker that identifies a cell as having undergone a recombinant DNA or RNA event. Selectable markers include, for example, genes that encode antimetabolite resistance such as the DHFR protein that confers resistance to methotrexate (Wigler et al, 1980, *Proc Natl Acad Sci USA* 77:3567; O'Hare et al., 1981, *Proc Natl Acad Sci USA*, 78:1527), the GPT protein that confers resistance to mycophenolic acid (Mulligan & Berg, 1981, *PNAS USA*, 78:2072), the neomycin resistance marker that confers resistance to the aminoglycoside G-418 (Calberre-Garapin et al., 1981, *J Mol Biol*, 150:1), the Hygro protein that confers resistance to hygromycin (Santerre et al., 1984, *Gene* 30:147), and the Zeocin™ resistance marker (Invitrogen). In addition, the herpes simplex virus thymidine kinase, hypoxanthine-guanine phosphoribosyltransferase and adenine phosphoribosyltransferase genes can be employed in tk$^-$, hgprt$^-$ and aprt$^-$ cells, respectively.

"Stringency" refers to the conditions (temperature, ionic strength, solvents, etc) under which hybridization between polynucleotides occurs. A hybridzation reaction conducted under high stringency conditions is one that will only occur between polynucleotide molecules that have a high degree of complementary base pairing (85% to 100% identity). Conditions for high stringency hybridization, for example, may include an overnight incubation at about 42° C. for about 2.5 hours in 6X SSC/0.1% SDS, followed by washing of the filters in 1.0×SSC at 65° C., 0.1% SDS. A hybridization reaction conducted under moderate stringency conditions is one that will occur between polynucleotide molecules that have an intermediate degree of complementary base pairing (50% to 84% identity).

"Substrate targeting moiety" refers to any signal on a substrate, either naturally occurring or genetically engineered, used to target any Gux1 polypeptide or fragment thereof to a substrate. Such targeting moieties include ligands that bind to a substrate structure. Examples of ligand/receptor pairs include carbohydrate binding domains and cellulose. Many such substrate-specific ligands are known and are useful in the present invention to target a Gux1 polypeptide or fragment thereof to a substrate. A novel example is a Gux1 carbohydrate binding domain that is used to tether other molecules to a cellulose-containing substrate such as a fabric.

"Thermal tolerant" refers to the property of withstanding partial or complete inactivation by heat and can also be described as thermal resistance or thermal stability. Although some variation exists in the literature, the following definitions can be considered typical for the optimum temperature range of stability and activity for enzymes: psychrophilic (below freezing to 10C.); mesophilic (10° C. to 50° C.); thermophilic (50° C. to 75° C.); and caldophilic (75° C. to above boiling water temperature). The stability and catalytic activity of enzymes are linked characteristics, and the ways of measuring these properties vary considerably. For industrial enzymes, stability and activity are best measured under use conditions, often in the presence of substrate. Therefore, cellulases that must act on process streams of cellulose must be able to withstand exposure up to thennophilic or even caldophilic temperatures for digestion times in excess of several hours.

In encompassing a wide variety of potential applications for embodiments of the present invention, thermal tolerance refers to the ability to function in a temperature range of from about 15° C. to about 100° C. A preferred range is from about 30° C. to about 80° C. A highly preferred range is from about 50° C. to about 70° C. For example, a protein that can function at about 45° C. is considered in the preferred range even though it may be susceptible to partial or complete inactivation at temperatures in a range above about 45° C. and less than about 80° C. For polypeptides derived from organisms such as *Acidothermus*, the desirable property of thermal tolerance among is often accompanied by other desirable characteristics such as: resistance to extreme pH degradation, resistance to solvent degradation, resistance to proteolytic degradation, resistance to detergent degradation, resistance to oxidizing agent degradation, resistance to chaotropic agent degradation, and resistance to general degradation. Cowan D A in Danson M J et al. (1992) *The Archaebacteria, Biochemistry and Biotechnology* at 149-159, University Press, Cambridge, ISBN 1855780100. Here 'resistance' is intended to include any partial or complete level of residual activity. When a polypeptide is described as thermal tolerant it is understood that any one, more than one, or none of these other desirable properties can be present.

"Variant", as used herein, means a polynucleotide or polypeptide molecule that differs from a reference molecule. Variants can include nucleotide changes that result in amino acid substitutions, deletions, fusions, or truncations in the resulting variant polypeptide when compared to the reference polypeptide.

"Vector," "extra-chromosomal vector" or "expression vector" refers to a first polynucleotide molecule, usually double-stranded, which may have inserted into it a second polynucleotide molecule, for example a foreign or heterologous polynucleotide. The heterologous polynucleotide molecule may or may not be naturally found in the host cell, and may be, for example, one or more additional copy of the heterologous polynucleotide naturally present in the host genome. The vector is adapted for transporting the foreign polynucleotide molecule into a suitable host cell. Once in the host cell, the vector may be capable of integrating into the host cell chromosomes. The vector may optionally contain additional elements for selecting cells containing the integrated polynucleotide molecule as well as elements to promote transcription of mRNA from transfected DNA. Examples of vectors useful in the methods of the present invention include, but are not limited to, plasmids, bacteriophages, cosmids, retroviruses, and artificial chromosomes.

Within the application, unless otherwise stated, the techniques utilized may be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in Methods in Enzymology (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols*, pp 109-128, ed. E. J. Murray, The Humana Press Inc., Clifton, N.J.).

O-Glycoside Hydrolases

Figure 2:
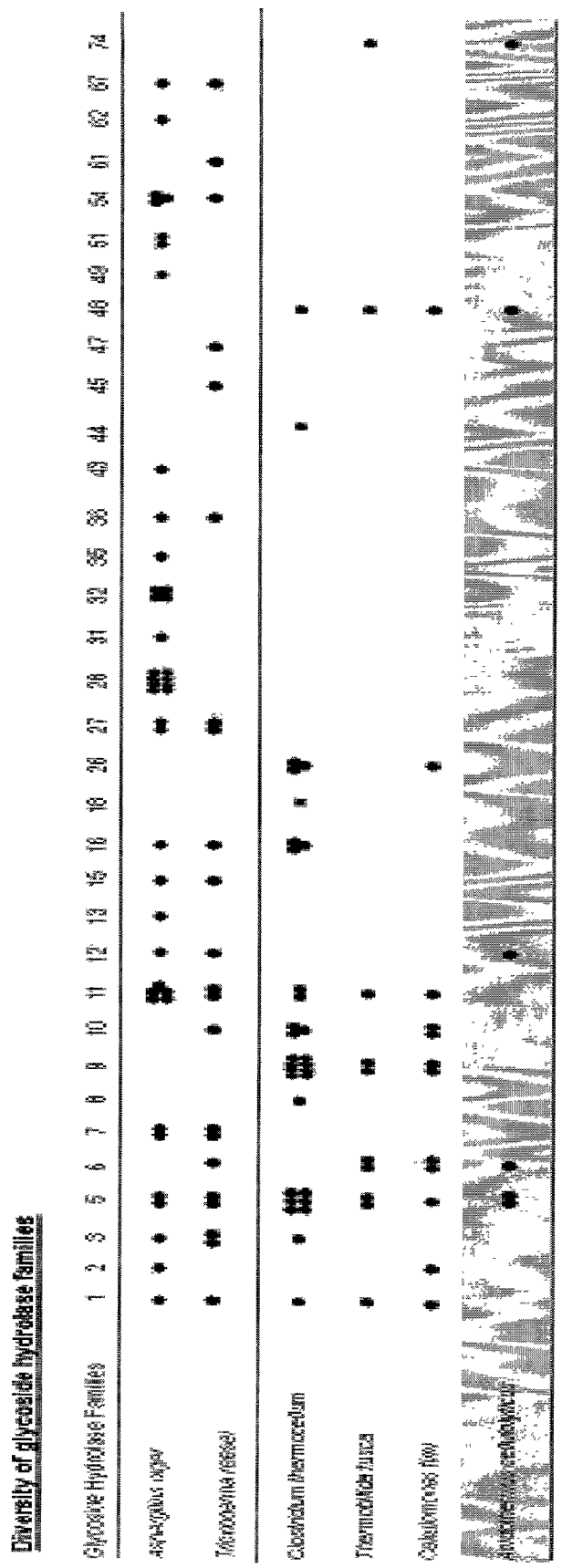
FIG. 2 is a graphic representation of the glycoside hydrolase gene/protein families found in various organisms.

Glycoside hydrolases are a large and diverse family of enzymes that hydrolyse the glycosidic bond between two carbohydrate moieties or between a carbohydrate and a non-carbohydrate moiety (See FIG. 2). Glycoside hydrolase enzymes are classified into glycoside hydrolase (GH) families based on significant amino acid similarities within their catalytic domains. Enzymes having related catalytic domains are grouped together within a family, (Hemrissat et al., (1991) supra, and Henrissat et al. (1996), Biochem. J. 316:695-696), where the underlying classification provides a direct relationship between the GH domain amino acid sequence and how a GH domain will fold. This information ultimately provides a common mechanism for how the enzyme will hydrolyse the glycosidic bond within a substrate, i.e., either by a retaining mechanism or inverting mechanism (Henrissat., B, (1991) supra).

Cellulases belong to the GH family of enzymes. Cellulases are produced by a variety of bacteria and fungi to degrade the beta-(1,4)-glycosidic bond of cellulose and to so produce successively smaller fragments of cellulose and ultimately produce glucose. At present, cellulases are found in at least 11 different GH families. Three different types of cellulase enzyme activities have been identified within these GH families: exo-acting cellulases which cleave successive disaccharide units from the non-reducing ends of a cellulose chain; endo-acting cellulases which randomly cleave successive disaccharide units within the cellulose chain; and β-glucosidases which cleave successive disaccharide units to glucose (J. W. Deacon, (1997) Modem Mycology, 3rd Ed., ISBN: 0-632-03077-1, 97-98).

Many cellulases are characterized by having a multiple domain unit within their overall structure, a GH or catalytic domain is joined to a carbohydrate-binding domain (CBD) by a glycosylated linker peptide (see FIG. 1) (Koivula et al., (1996) Protein Expression and Purification 8:391-400). As noted above, cellulases do not belong to any one family of GH domains, but rather have been identified within at least 11 different GH families to date. The CBD type domain increases the concentration of the enzyme on the substrate, in this case cellulose, and the linker peptide provides flexibility for both larger domains.

Conversion of cellulose to glucose is an essential step in the production of ethanol or other biofuels from biomass. Cellulases are an important component of this process, where approximately one kilogram of cellulase can digest fifty kilograms of cellulose. Within this process, thermostable cellulases have taken precedent, due to their ability to function at elevated temperatures and under other conditions including pH extremes, solvent presence, detergent presence, proteolysis, etc. (see Cowan D A (1992), supra).

Highly thermostable cellulase enzymes are secreted by the cellulolytic themophile *Acidothermus cellulolyticus* (U.S. Pat. Nos. 5,275,944 and 5,110,735). This bacterium was originally isolated from decaying wood in an acidic, thermal pool at Yellowstone National Park and deposited with the American Type Culture Collection (ATCC 43068) (Mohagheghi et al., (1986) *Int. J. System. Bacteriol.*, 36:435-443).

Recently, a thermostable cellulase, E1 endoglucanase, was identified and characterized from *Acidothermus cellulolyticus* (U.S. Pat. No. 5,536,655). The E1 endoglucanase has maximal activity between 75 and 83° C. and is active to a pH well below 5. Thermostable cellulase, and E1 endoglucanase, are useful in the conversion of biomass to biofuels, and in particular, are useful in the conversion of cellulose to glucose. Conversion of biomass to biofuel represents an extremely important alternative fuel source that is more environmentally friendly than conventional fuels, and provides a use, in some cases, for waste products.

Gux1

As described more fully in the Examples below, Gux1, a novel thermostable cellulase, has now been identified and characterized. The predicted amino acid sequence of Gux1 (SEQ ID NO: 1) has an organization characteristic of a cellulase enzyme. Gux1 contains a carbohydrate binding domain-linker domain-catalytic domain-linker domain-fibronectin domain-linker domain-carbohydrate binding domain unit. In particular, a catalytic domain unit includes a carbohydrate binding domain type III (amino acids from about A35 to about A187), a GH48 catalytic domain (amino acids from about N231 to about P870), and a $CBD_{II}$ (amino acids from about G1021 to about S1121). As discussed in more detail below, significant amino acid similarity of Gux1 to other cellulases identifies Gux1 as a cellulase.

Gux1, as noted above, has a catalytic domain, identified as belonging to the GH48 family. The GH48 domain family includes a number of exoglucanases, for example, from *Cellulomonas fimi*, and exoglucanase E6 isolated from *Thermobifida fusca*. The GH48 members degrade substrate using an inverting mechanism. Being a member of the GH48 family of proteins identifies Gux1 as potentially having exoglucanase activity. In addition, the predicted amino acid sequence (SEQ ID NO: 1) indicates that CBD type II and CBD type III domains are present as characterized by Tomme P. et al. (1995), in Enzymatic Degradation of Insoluble Polysaccharides (Saddler J N & Penner M, eds.), at 142-163, American Chemical Society, Washington. See also Tomme, P. & Claeyssens, M. (1989) FEBS Lett. 243, 239-2431; Gilkes, N. R et al., (1988) J.Biol.Chem. 263, 10401-10407.

Gux1 is also a thermostable cellulase as it is produced by the themophile *Acidothermus cellulolyticus*. As discussed, Gux1 polypeptides can have other desirable characteristics (see Cowan D A (1992), supra). Like other members of the cellulase family, and in particular thermostable cellulases, Gux1 polypeptides are useful in the conversion of biomass to biofuels and biofuel additives, and in particular, biofuels from cellulose. It is envisioned that Gux1 polypeptides could be used for other purposes, for example in detergents, pulp and paper processing, food and feed processing, and in textile processes. Gux1 polypeptides can be used alone or in combination with one or more other cellulases or glycoside hydrolases to perform the uses described herein or known within the relevant art, all of which are within the scope of the present disclosure.

Gux1 Polypeptides

Gux1 polypeptides of the invention include isolated polypeptides having an amino acid sequence as shown below in Example 1; Table 1 and in SEQ ID NO: 1, as well as variants and derivatives, including fragments, having substantial identity to the amino acid sequence of SEQ ID NO: 1 and that retain any of the functional activities of Gux1. Gux1 polypeptide activity can be determined, for example, by subjecting the variant, derivative, or fragment to a substrate binding assay or a cellulase activity assay such as those described in Irwin D et al., J. Bacteriology 180(7): 1709-1714 (April 1998).

TABLE 1

Gux1 amino acid sequence (SEQ ID NO:1)
MPGLRRRLPAGIVSAAALGSLVS-
GLVAVAPVAHAAVTLKAQYKNND-
SAPS
DNQIKPGLQLVNTGSSSVDL-
STVTVRYWFTRDGGSSTLVYNCD-
WAAMGCG
NIRASFGSVNPATPTADTYLQLS-
FTGGTLAAGGSTGEIQNRVNKSD-
WSNF
DETNDYSYGTNTTFQDWT-
KVTVYVNGVLVWGTEPSGATASP-
SASATPSPS
SSPTTSPSSSPSPSSSPTPTPSSSSPPPSSNDPYIQRFLTMYNKIHDPAN
GYFSPQGIPYHSVETLIVEAP-
DYGHETTSEAYSFWLWLEATYGA-
VTGNWT
PFNNAWTTMETYMIPQHADQPN-
NASYNPNSPASYAPEE-
PLPSMYPVAIDS
SVPVGHDPLAAELQSTYGTPDIYG-
MHWLADVDNIYGYGDSPGGGCEL-
GPS
AKGVSYINTFQRGSQES-
VWETVTQPTCDNGKYGGAH-
GYVDLFIQGSTPPQ
WKYTDAPDADARAVQAAYWAYT-
WASAQGKASAIAPTIAKASQT-
GDYLRYS
LFDKYFKQVGNCYPASSCPGAT-
GRQSETYLIGWYYAWGGSSQG-
WAWRIGD
GAAHFGYQNPLAAWAMSNVTPLI-
PLSPTAKSDWAASLQRQLE-
FYQWLQSA
EGAIAGGATNSWNGNYGTPPAGD-
STFYGMAYDWEPVYHDPPSNNWFG-
FQA
WSMERVAEYYYVTGDPKAKALLDK-
WVAWVKPNVTTGASW-
SIPSNLSWSGQ
PDTWNPSNPGTNANLHVTITSS-
GQDVGVAAALAKTLEYYAAKSGD-
TASRD
LAKGLLDSMWNNDQDSLGVSTPE-
TRTDYSRFTQVYDPTTGDGLYIPS-
GWT
GTMPNGDQIKPGATFLSIRSWYT-
KDPQWSKVQAYLNGGPAPTFNYHR-
FWA
ESDFAMANADFGMLFPSG-
SPSPTPSPTPTSSPSPTPSSSPTPSPSPSPTG
DTTPPSVPTGLQVTGTTTSS-
VSLSWTASTDNVGVAHYN-
VYRNGTLVGQPT
ATSFTDTGLAAGTSY-
TYTVAAVDAAGNTSAQSFAGDS-
DDGIAVASPSPSP TABLE 1-continued

```
TPTSSPSPTPSPTPSPTSTSGASC-
TATYVVNSDWGSGFTTTVTVTNT-
GTR
ATSGWTVTWSFAGNQTVTNYWN-
TALTQSGKSVTAKNLSYN-
NVIQPGQSTT
FGFNGSYSGTNTAPTLSCTAS
```

As listed and described in Tables 1 and 5, the isolated Gux1 polypeptide includes an N-terminal hydrophobic region that functions as a signal peptide, having an amino acid sequence that begins with Met1 and extends to about A34; a carbohydrate binding domain having sequence similarity to such type III domains that begins with about A35 and extends to about A187, a catalytic domain having significant sequence similarity to a GH48 family domain that begins with about N231 and extends to about P870, a fibronectin type III domain that begins with about D901 and extends to about G985, a carbohydrate binding domain type II region that begins with about G1021 and extends to about S1121. Variants and derivatives of Gux1 include, for example, Gux1 polypeptides modified by covalent or aggregative conjugation with other chemical moieties, such as glycosyl groups, polyethylene glycol (PEG) groups, lipids, phosphate, acetyl groups, and the like.

The amino acid sequence of Gux1 polypeptides of the invention is preferably at least about 60% identical, more preferably at least about 70% identical, or in some embodiments at least about 90% identical, to the Gux1 amino acid sequence shown above in Table 1 and SEQ ID NO: 1. The percentage identity, also termed homology (see definition above) can be readily determined, for example, by comparing the two polypeptide sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman, 1981, *Adv. Appl. Math.* 2: 482-489.

Variants and derivatives of the Gux1 polypeptide may further include, for example, fusion proteins formed of a Gux1 polypeptide and a heterologous polypeptide. Preferred heterologous polypeptides include those that facilitate purification, oligomerization, stability, or secretion of the Gux1 polypeptides.

Gux1 polypeptide fragments may include, but are not limited to, the polypeptide sequences listed in Table 4, SEQ ID NOS: 3, 4, 5, 6, and 7.

Gux1 polypeptide variants and derivatives, as used in the description of the invention, can contain conservatively substituted amino acids, meaning that one or more amino acid can be replaced by an amino acid that does not alter the secondary and/or tertiary structure of the polypeptide. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Phenotypically silent amino acid exchanges are described more fully in Bowie et al., 1990, *Science* 247:1306-1310. In addition, functional Gux1 polypeptide variants include those having amino acid substitutions, deletions, or additions to the amino acid sequence outside functional regions of the protein, for example, outside the catalytic and carbohydrate binding domains. These would include, for example, the various linker sequences that connect functional domains as defined herein.

The Gux1 polypeptides of the present invention are preferably provided in an isolated form, and preferably are substantially purified. The polypeptides may be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. Preferably, high performance liquid chromatography (HPLC) is employed for purification.

Another preferred form of Gux1 polypeptides is that of recombinant polypeptides as expressed by suitable hosts. Furthermore, the hosts can simultaneously produce other cellulases such that a mixture is produced comprising a Gux1 polypeptide and one or more other cellulases. Such a mixture can be effective in crude fermentation processing or other industrial processing.

Gux1 polypeptides can be fused to heterologous polypeptides to facilitate purification. Many available heterologous peptides (peptide tags) allow selective binding of the fusion protein to a binding partner. Non-limiting examples of peptide tags include 6-His (SEQ ID NO: 8), thioredoxin, hemaglutinin, GST, and the OmpA signal sequence tag. A binding partner that recognizes and binds to the heterologous peptide can be any molecule or compound, including metal ions (for example, metal affinity columns), antibodies, antibody fragments, or any protein or peptide that preferentially binds the heterologous peptide to permit purification of the fusion protein.

Gux1 polypeptides can be modified to facilitate formation of Gux1 oligomers. For example, Gux1 polypeptides can be fused to peptide moieties that promote oligomerization, such as leucine zippers and certain antibody fragment polypeptides, for example, Fc polypeptides. Techniques for preparing these fusion proteins are known, and are described, for example, in WO 99/31241 and in Cosman et. al., 2001 *Immunity* 14:123-133. Fusion to an Fc polypeptide offers the additional advantage of facilitating purification by affinity chromatography over Protein A or Protein G columns. Fusion to a leucine-zipper (LZ), for example, a repetitive heptad repeat, often with four or five leucine residues interspersed with other amino acids, is described in Landschultz et al., 1988, *Science*, 240:1759.

It is also envisioned that an expanded set of variants and derivatives of Gux1 polynucleotides and/or polypeptides can be generated to select for useful molecules, where such expansion is achieved not only by conventional methods such as site-directed mutagenesis (SDM) but also by more modern techniques, either independently or in combination.

Site-directed-mutagenesis is considered an informational approach to protein engineering and can rely on high-resolution crystallographic structures of target proteins and some stratagem for specific amino acid changes (Van Den Burg, B.; Vriend, G.; Veltman, O. R.; Venema, G.; Eijsink, V. G. H. Proc. Nat. Acad. Sci. U.S. 1998, 95, 2056-2060). For example, modification of the amino acid sequence of Gux1 polypeptides can be accomplished as is known in the art, such as by introducing mutations at particular locations by oligo-nucleotide-directed mutagenesis (Walder et al.,1986, Gene, 42:133; Bauer et al., 1985, Gene 37:73; Craik, 1985, Bio-Techniques, 12-19; Smith et al., 1981, Genetic Engineering: Principles and Methods, Plenum Press; and U.S. Pat. No. 4,518,584 and U.S. Pat. Nos. 4,737,462). SDM technology can also employ the recent advent of computational methods for identifying site-specific changes for a variety of protein engineering objectives (Hellinga, H. W. Nature Structural. Biol. 1998, 5, 525-527).

The more modem techniques include, but are not limited to, non-informational mutagenesis techniques (referred to generically as "directed evolution"). Directed evolution, in conjunction with high-throughput screening, allows testing of statistically meaningful variations in protein conformation (Arnold, F. H. Nature Biotechnol. 1998, 16, 617-618). Directed evolution technology can include diversification methods similar to that described by Crameri A. et al. (1998, Nature 391: 288-291), site-saturation mutagenesis, staggered extension process (StEP) (Zhao, H.; Giver, L.; Shao, Z.; Affholter, J. A.; Arnold, F. H. Nature Biotechnol. 1998, 16, 258-262), and DNA synthesis/reassembly (U.S. Pat. No. 5,965,408).

Fragments of the Gux1 polypeptide can be used, for example, to generate specific anti-Gux1 antibodies. Using known selection techniques, specific epitopes can be selected and used to generate monoclonal or polyclonal antibodies. Such antibodies have utlilty in the assay of Gux1 activity as well as in purifying recombinant Gux1 polypeptides from genetically engineered host cells.

Gux1 Polynucleotides

The invention also provides polynucleotide molecules encoding the Gux1 polypeptides discussed above. Gux1 polynucleotide molecules of the invention include polynucleotide molecules having the nucleic acid sequence shown in Table 2 and SEQ ID NO: 2, polynucleotide molecules that hybridize to the nucleic acid sequence of Table 2 and SEQ ID NO: 2 under high stringency hybridization conditions (for example, 42°, 2.5 hr., 6×SCC, 0.1% SDS); and polynucleotide molecules having substantial nucleic acid sequence identity with the nucleic acid sequence of Table 2 and SEQ ID NO: 2, particularly with those nucleic acids encoding the catalytic domain, GH48 (from about amino acid N231 to about P870), the carbohydrate binding domain III (from about amino acid A35 to A187) and carbohydrate binding domain II (from about G1021 to about amino acid S1121).

TABLE 2

```
Gux1 nucleotide sequence                                                (SEQ ID NO:2).
ATGCCAGGATTACGACGGCGACTCCGCGCCGGTATCGTCTCGGCGGCGGCGTTGGGGTCGCTGGTTAGCGG

GCTCGTTGCCGTCGCACCAGTCGCGCACGCGGCGGTGACTCTCAAAGCGCAGTATAAGAACAATGATTCGG

CGCCGAGTGACAACCAGATCAAACCGGGTCTCCAGTTGGTGAATACCGGGTCGTCGTCGGTGGAUTGTCG

ACGGTGACGGTGCGGTACTGGTTCACCCGGGATGGTGGGTCGTCGACACTGGTGTACAACTGTGACTGGGC

GGCGATGGGGTGTGGGAATATCCGCGCCTCGTTCGGCTCGGTGAACCCGGCGACGCCGACGGCGGACACC

TACCTGCAGTTGTCGTTCACTGGTGGAACGTTGGCCGCTGGTGGGTCGACGGGTGAGATTCAAAACCGGGT

GAATAAGAGTGACTGGTCGAACTTTGATGAGACCAATGACTACTCGTATGGGACGAACACCACCTTCCAGG

ACTGGACGAAGGTGACGGTGTACGTCAACGGCGTGTTGGTCTGGGGGACCGAACCGTCCGGAGCGACGGC

GTCTCCATCCGCGTCGGCGACGCCCAGCCCGTCCAGTTCACCGACCACGAGTCCGAGTTCGTCCCCGTCGCC

GAGCAGCAGCCCGACGCCGACACCGAGCAGCTCGTCGCCGCCCGTCGTCCAACGACCCGTACATCCAGCG

GTTCCTCACGATGTACAACAAGATTCACGACCCAGCGAACGGCTACTTCAGCCCGCAGGGAATTCCCTACC

ACTCGGTAGAAACGCTCATCGTTGAGGCACCGGACTACGGGCACGAGACAACTTCGGAGGCGTACAGCTTC

TGGCTCTGGCTCGAAGCGACGTACGGCGCAGTGACCGGCAACTGGACGCCGTTCAACAACGCCTGGACGAC

GATGGAAACGTACATGATGCCGCAGCAGGCGGACCAGCCGAACAACGCGTCGTACAACCCCAACAGCCCG

GCGTCGTACGCTCCGGAAGAGCCGCTGCCCAGCATGTACCCGGTTGCCATCGACAGCAGCGTGCCGGTTGG

GCACGACCCGCTCGCCGCCGAATTGCAGTCGACGTACGGCACTCCGGACATTTACGGCATGCACTGGCTGG

CCGACGTTGACAACATCTACGGATACGGCGACAGCCCCGGCGGTGGTTGCGAACTCGGTCCTTCCGCTAAG

GGCGTCTCCTACATCAACACATTCCAGCGCGGCTCGCAGGAGTCCGTCTGGGAGACGGTCACCCAGCCGAC

GTGCGACAACGGCAAGTACGGTGGGCGCACGGCTACGTCGACCTGTTCATCCAGGGTTCGACGCCGCCGC

AGTGGAAGTACACCGATGCCCCGGACGCCGACGCCCGTGCCGTCCAGGCTGCGTACTGGGCCTACACCTGG

GCATCGGCGCAGGGCAAGGCAAGCGCGATTGCCCCGACGATCGCCAAGGCGAGCCAAACCGGCGACTACC

TGCGGTACTCGCTCTTTGACAAGTACTTCAAGCAGGTCGGCAACTGCTACCCGGCCAGCTCCTGCCCTGGA

GCAACCGGACGCCAGAGCGAGACCTACCTGATCGGCTGGTACTACGCCTGGGGCGGCTCAAGCCAAGGCT

GGGCCTGGCGCATTGGTGACGGCGCCGCGCACTTCGGCTACCAGAATCCGCTTGCCGCGTGGGCGATGTCG

AACGTGACACCGCTCATTCCGCTCTCGCCCACGGCAAAGAGCGACTGGGCGGCGAGCTTGCAGCGCCAGCT

GGAGTTCTACCAGTGGTTGCAATCCGCGGAAGGAGCCATTGCGGGCGGCGCCACCAACAGCTGGAACGGC
```

TABLE 2-continued

```
AATTACGGGACCCCGCCGGCCGGAGACTCGACCTTCTACGGCATGGCGTACGACTGGGAGCCGGTCTACCA
CGACCCGCCGAGCAACAACTGGTTCGGCTTCCAGGCGTGGTCCATGGAACGGGTTGCCGAGTACTACACG
TCACCGGCGACCCGAAGGCCAAGGCGCTGCTCGACAAGTGGGTCGCATGGGTGAAGCCGAATGTCACCAC
CGGTGCCTCATGGTCGATTCCGTCGAATTTGTCCTGGAGCGGCCAACCGGATACCTGGAATCCGAGCAACC
CAGGAACGAATGCCAACCTGCACGTGACCATCACGTCGTCCGGGCAGGACGTCGGTGTTGCCGCGGCGCTC
GCGAAGACACTCGAGTACTACGCGGCAAAATCCGGCGATACGGCCTCGCGCGACCTCGCGAAGGGATTGC
TCGACTCCATGTGGAACAACGACCAGGACAGCCTCGGTGTGAGCACACCGGAGACGCGGACCGACTACTCT
CGGTTCACTCAGGTGTAGGACCCGACGACTGGTGACGGCCTCTACATCCCGTCGGGTTGGACGGGGACCAT
GCCCAACGGTGACCAAATCAAGCCGGGTGCGACCTTCCTGAGCATCCGGTCCTGGTACACCAAGGATCCGC
AGTGGTCGAAGGTGCAGGCGTACCTCAACGGCGGGCCTGCTCCGACGTTCAACTACCACCGGTTCTGGGCG
GAGTCGGACTTCGCGATGGCGAACGCCGATTTTGGCATGCTCTTCCCATCCGGGTCGCCCAGCCCGACCCC
GAGCCCGACTCCGACGTCGTCCCCGAGCCCGACTCCGAGCAGCTCGCCGACGCCGTCGCCCAGCCCGTCAC
CGACCGGCGACACCACGCCGCCGAGCGTGCCGACGGGTCTTCAGGTCACCGGGACAACGACGTCGTCCGTG
TCGCTCAGCTGGACCGCGTCCACCGACAACGTCGGCGTCGCGCACTACAACGTGTACCGAAACGGCACGCT
GGTGGGTCAGCCGACAGCGACGTCGTTCACGGACACCGGCCTGGCTGCTGGCACGTCGTACACGTACACAG
TGGCGGCCGTTGATGCGGCCGGTAACACGTCGGCGCAGAGCTTCGCCGGTGACAGCGACGACGGCATCGC
CGTCGCGAGCCCGTCGCCGAGCCCGACTCCGACGTCGTCCCCGAGCCCAACGCCGTCGCCGACACCGTCAC
CGACGTCCACCAGCGGCGCATCGTGCACTGCTACCTACGTTGTCAATAGCGACTGGGGTAGCGGCTTCACG
ACAACCGTGACCGTGACGAACACCGGGACCAGGGCCACCAGTGGCTGGACGGTCACGTGGAGCTTTGCCG
GTAATCAGACGGTCACCAACTACTGGAACACCGCGCTGACGCAATCCGGAAAGTCGGTGACCGCAAAGAA
CCTGAGTTACAACAACGTCATCCAACCTGGTCAGTCGACGACCTTTGGATTCAACGGAAGTTACTGAGGAA
CAAACACCGCGCCGACGCTCAGCTGCACGGCAAGCTGA
```

The Gux1 polynucleotide molecules of the invention are preferably isolated molecules encoding the Gux1 polypetide having an amino acid sequence as shown in Table I and SEQ ID NO: 1, as well as derivatives, variants, and useful fragments of the Gux1 polynucleotide. The Gux1 polynucleotide sequence can include deletions, substitutions, or additions to the nucleic acid sequence of Table 2 and SEQ ID NO: 2.

The Gux1 polynucleotide molecule of the invention can be cDNA, chemically synthesized DNA, DNA amplified by PCR, RNA, or combinations thereof. Due to the degeneracy of the genetic code, two DNA sequences may differ and yet encode identical amino acid sequences. The present invention thus provides an isolated polynucleotide molecule having a Gux1 nucleic acid sequence encoding Gux1 polypeptide, where the nucleic acid sequence encodes a polypeptide having the complete amino acid sequences as shown in Table 1 and SEQ ID NO: 1, or variants, derivatives, and fragments thereof.

The Gux1 polynucleotides of the invention have a nucleic acid sequence that is at least about 60% identical to the nucleic acid sequence shown in Table 2 and SEQ ID NO: 2, in some embodiments at least about 70% identical to the nucleic acid sequence shown in Table 2 and SEQ ID NO: 2, and in i other embodiments at least about 90% identical to the nucleic acid sequence shown in Table 2 and SEQ ID NO: 2. Nucleic acid sequence identity is determined by known methods, for example by aligning two sequences in a software program such as the BLAST program (Altschul, S. F et al. (1990) J. Mol. Biol. 215:403-410, from the National Center for Biotechnology Information (http://www.ncbi.nhn.nih.gov/BLAST/).

The Gux1 polynucleotide molecules of the invention also include isolated polynucleotide molecules having a nucleic acid sequence that hybridizes under high stringency conditions (as defined above) to a the nucleic acid sequence shown in Table 2 and SEQ ID NO: 2. Hybridization of the polynucleotide is to at least about 15 contiguous nucleotides, or at least about 20 contiguous nucleotides, and in other embodiments at least about 30 contiguous nucleotides, and in still other embodiments at least about 100 contiguous nucleotides of the nucleic acid sequence shown in Table 2 and SEQ ID NO: 2.

Useful fragments of the Gux1-encoding polynucleotide molecules described herein, include probes and primers. Such probes and primers can be used, for example, in PCR methods to amplify and detect the presence of Gux1 polynucleotides in vitro, as well as in Southern and Northern blots for analysis of Gux1. Cells expressing the Gux1 polynucleotide molecules of the invention can also be identified by the use of such probes. Methods for the production and use of such primers and probes are known. For PCR, 5' and 3' primers corresponding to a region at the termini of the Gux1 polynucleotide molecule can be employed to isolate and amplify the Gux1 polynucleotide using conventional techniques.

Other useful fragments of the Gux1 polynucleotides include antisense or sense oligonucleotides comprising a single-stranded nucleic acid sequence capable of binding to a target Gux1 mRNA (using a sense strand), or DNA (using an antisense strand) sequence.

Vectors and Host Cells

The present invention also provides vectors containing the polynucleotide molecules of the invention, as well as host cells transformed with such vectors. Any of the polynucleotide molecules of the invention may be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the Gux1 polynucleotide molecule. Examples of such regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a Gux1 DNA sequence if the promoter nucleotide sequence directs the transcription of the Gux1 sequence.

Selection of suitable vectors for the cloning of Gux1 polynucleotide molecules encoding the target Gux1 polypeptides of this invention will depend upon the host cell in which the vector will be transformed, and, where applicable, the host cell from which the target polypeptide is to be expressed. Suitable host cells for expression of Gux1 polypeptides include prokaryotes, yeast, and higher eukaryotic cells, each of which is discussed below.

The Gux1 polypeptides to be expressed in such host cells may also be fusion proteins that include regions from heterologous proteins. As discussed above, such regions may be included to allow, for example, secretion, improved stability, or facilitated purification of the Gux1 polypeptide. For example, a nucleic acid sequence encoding an appropriate signal peptide can be incorporated into an expression vector. A nucleic acid sequence encoding a signal peptide (secretory leader) may be fused in-frame to the Gux1 sequence so that Gux1 is translated as a fusion protein comprising the signal peptide. A signal peptide that is functional in the intended host cell promotes extracellular secretion of the Gux1 polypeptide. Preferably, the signal sequence will be cleaved from the Gux1 polypeptide upon secretion of Gux1 from the cell. Non-limiting examples of signal sequences that can be used in practicing the invention include the yeast I-factor and the honeybee melatin leader in Sf9 insect cells.

Suitable host cells for expression of target polypeptides of the invention include prokaryotes, yeast, and higher eukaryotic cells. Suitable prokaryotic hosts to be used for the expression of these polypeptides include bacteria of the genera Escherichia, Bacillus, and Salmonella, as well as members of the genera Pseudomonas, Streptomyces, and Staphylococcus. For expression in prokaryotic cells, for example, in $E.$ $coli$, the polynucleotide molecule encoding Gux1 polypeptide preferably includes an N-terminal methionine residue to facilitate expression of the recombinant polypeptide. The N-terminal Met may optionally be cleaved from the expressed polypeptide.

Expression vectors for use in prokaryotic hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pSPORT vectors, pGEM vectors (Promega, Madison, Wis.), pPROEX vectors (LTI, Bethesda, Md.), Bluescript vectors (Stratagene), and pQE vectors (Qiagen).

Gux1 can also be expressed in yeast host cells from genera including $Saccharomyces$, $Pichia$, and $Kluveromyces$. Preferred yeast hosts are $S.$ $cerevisiae$ and $P.$ $pastoris$. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and $E.$ $coli$ (termed shuttle vectors) may also be used. In addition to the above-mentioned features of yeast vectors, a shuttle vector will also include sequences for replication and selection in $E.$ $coli$. Direct secretion of the target polypeptides expressed in yeast hosts may be accomplished by the inclusion of nucleotide sequence encoding the yeast I-factor leader sequence at the 5' end of the Gux1-encoding nucleotide sequence.

Insect host cell culture systems can also be used for the expression of Gux1 polypeptides. The target polypeptides of the invention are preferably expressed using a baculovirus expression system, as described, for example, in the review by Luckow and Summers, 1988 $Bio/Technology$ 6:47.

The choice of a suitable expression vector for expression of Gux1 polypeptides of the invention will depend upon the host cell to be used. Examples of suitable expression vectors for $E.$ $coli$ include pET, pUC, and similar vectors as is known in the art. Preferred vectors for expression of the Gux1 polypeptides include the shuttle plasmid pIJ702 for $Streptomyces$ $lividans$, pGAPZalpha-A, B, C and pPICZalpha-A, B, C (Invitrogen) for $Pichia$ $pastoris$, and pFE-1 and pFE-2 for filamentous fungi and similar vectors as is known in the art.

Modification of a Gux1 polynucleotide molecule to facilitate insertion into a particular vector (for example, by modifying restriction sites), ease of use in a particular expression system or host (for example, using preferred host codons), and the like, are known and are contemplated for use in the invention. Genetic engineering methods for the production of Gux1 polypeptides include the expression of the polynucleotide molecules in cell free expression systems, in cellular hosts, in tissues, and in animal models, according to known methods.

Compositions

The invention provides compositions containing a substantially purified Gux1 polypeptide of the invention and an acceptable carrier. Such compositions are administered to biomass, for example, to degrade the cellulose in the biomass into simpler carbohydrate units and ultimately, to sugars. These A released sugars from the cellulose are converted into ethanol by any number of different catalysts. Such compositions may also be included in detergents for removal, for example, of cellulose containing stains within fabrics, or compositions used in the pulp and paper industry, to address conditions associated with cellulose content. Compositions of the present invention can be used in stonewashing jeans such as is well known in the art. Compositions can be used in the biopolishing of cellulosic fabrics, such as cotton, linen, rayon and Lyocell.

The invention provides pharmaceutical compositions containing a substantially purified Gux1 polypeptide of the invention and if necessary a pharmaceutically acceptable carrier. Such pharmaceutical compositions are administered to cells, tissues, or patients, for example, to aid in delivery or targeting of other pharmaceutical compositions. For example, Gux1 polypeptides may be used where carbohydrate-mediated liposomal interactions are involved with target cells. Vyas S P et al. (2001), J. Pharmacy & Pharmaceutical Sciences May-August 4(2): 138-58.

The invention also provides reagents, compositions, and methods that are useful for analysis of Gux1 activity and for the analysis of cellulose breakdown.

Compositions of the present invention may also include other known cellulases, and preferably, other known thermal tolerant cellulases for enhanced treatment of cellulose.

Antibodies

The polypeptides of the present invention, in whole or in part, may be used to raise polyclonal and monoclonal antibodies that are useful in purifying Gux1, or detecting Gux1 polypeptide expression, as well as a reagent tool for characterizing the molecular actions of the Gux1 polypeptide. Preferably, a peptide containing a unique epitope of the Gux1 polypeptide is used in preparation of antibodies, using conventional techniques. Methods for the selection of peptide epitopes and production of antibodies are known. See, for example, *Antibodies: A Laboratory Manual*, Harlow and Land (eds.), 1988 Cold Spring Harbor Laboratory Press, Cold Spring Harbor, N.Y.; *Monoclonal Antibodies, Hybridomas: A New Dimension in Biological Analyses*, Kennet et al. (eds.), 1980 Plenum Press, New York.

Assays

Agents that modify, for example, increase or decrease, Gux1 hydrolysis or degradation of cellulose can be identified, for example, by assay of Gux1 cellulase activity and/or analysis of Gux1 binding to a cellulose substrate. Incubation of cellulose in the presence of Gux1 and in the presence or absence of a test agent and correlation of cellulase activity or carbohydrate binding permits screening of such agents. For example, cellulase activity and binding assays may be performed in a manner similar to those described in Irwin et al., J. Bacteriology 180(7): 1709-1714 (April 1998).

The Gux1 stimulated activity is determined in the presence and absence of a test agent and then compared. A lower Gux1 activated test activity in the presence of the test agent, than in the absence of the test agent, indicates that the test agent has decreased the activity of the Gux1. A higher Gux1 activated test activity in the presence of the test agent than in the absence of the test agent indicates that the test agent has increased the activity of the Gux1. Stimulators and inhibitors of Gux1 may be used to augment, inhibit, or modify Gux1 mediated activity, and therefore may have potential industrial uses as well as potential use in the further elucidation of Gux1's molecular actions.

Therapeutic Applications

The Gux1 polypeptides of the invention are effective in adding in delivery or targeting of other pharmaceutical compositions within a host. For example, Gux1 polypeptides may be used where carbohydrate-mediated liposomal interactions are involved with target cells. Vyas S P et al. (2001), *J. Pharm Pharm Sci* May-August 4(2): 138-58.

Gux1 polynucleotides and polypeptides, including vectors expressing Gux1, of the invention can be formulated as pharmaceutical compositions and administered to a host, preferably mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

Gux1 can be administered by known techniques, such as orally, parentally (including subcutaneous injection, intravenous, intramuscular, intrastemal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or rev subcutaneous routes. More preferably, the compounds of the present invention are administered parenterally, i.e., intravenously or intraperitoneally, by infusion or injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Industrial Applications

The Gux1 polypeptides of the invention are effective cellulases. In the methods of the invention, the cellulose degrading effects of Gux1 are achieved by treating biomass at a ratio of about 1 to about 50 of Gux1:biomass. Gux1 may be used under extreme conditions, for example, elevated temperatures and acidic pH. Treated biomass is degraded into simpler forms of carbohydrates, and in some cases glucose, which is then used in the formation of ethanol or other industrial chemicals, as is known in the art. Other methods are envisioned to be within the scope of the present invention, including methods for treating fabrics to remove cellulose-containing stains and other methods already discussed. Gux1 polypeptides can be used in any known application currently utilizing a cellulase, all of which are within the scope of the present invention.

Having generally described the invention, the same will be more readily understood by reference to the following examples, which are provided by way of illustration and are not intended as limiting.

EXAMPLES

Example 1

Molecular Cloning of Gux1

Genomic DNA was isolated from *Acidothermus cellulolyticus* and purified by banding on cesium chloride gradients. Genomic DNA was partially digested with Sau 3A and separated on agarose gels. DNA fragments in the range of 9-20 kilobase pairs were isolated from the gels. This purified Sau 3A digested genomic DNA was ligated into the Bam H1 acceptor site of purified EMBL3 lambda phage arms (Clontech, San Diego, Calif.). Phage DNA was packaged according to the manufacturer's specification and plated with *E. Coli* LE392 in top agar which contained the soluble cellulose analog, carboxymethylcellulose (CMC). The plates were incubated overnight (12-24 hours) to allow transfection, bacterial growth, and plaque formation. Plates were stained with Congo Red followed by destaining with 1 M NaCl. Lambda plaques harboring endoglucanase clones showed up as unstained plaques on a red background.

Lambda clones which screened positive on CMC-Congo Red plates were purified by successive rounds of picking, plating and screening. Individual phage isolates were named SL-1, SL-2, SL-3, and SL-4. Subsequent subcloning efforts employed the SL-3 clone which contained an approximately 14.2 kilobase fragment of *Acidothermus cellulolyticus* genomic DNA.

Template DNA was constructed using a 9 kilobase Bam H1 fragment obtained from the 14.2 kilobase lambda clone SL-3 prepared from *Acidothermus cellulolyticus* genomic DNA. The 9 kilobase Bam H1 fragment from SL-3 was subcloned into pDR540 to generate a plasmid NREL501. NREL501 was sequenced by the primer walking method as is known in the art. NREL501 was then subcloned into pUC19 using restriction enzymes Pst I and Eco RI and transformed into *E. coli* XL1-blue (Stratagene) for the production of template DNA for sequencing. Each subclone was sequenced from both the forward and reverse directions. DNA for sequencing was prepared from an overnight growth in 500 mL LB broth using a megaprep DNA purification kit from Promega. The templated DNA was PEG precipitated and suspended in de-ionized water and adjusted to a final concentration of 0.25 milligrams/mL.

Custom primers were designed by reading upstream known sequence and selecting segments of an appropriate length to function, as is well known in the art. Primers for cycle sequencing were synthesized at the Macromolecular Resources Facility located at Colorado State University in Fort Collins, Colo. Typically the sequencing primers were 26 to 30 nucleotides in length, but were sometimes longer or shorter to accommodate a melting temperature appropriate for cycle sequencing. The sequencing primers were diluted in de-ionized water, the concentration measured using UV absorbance at 260 nm, and then adjusted to a final concentration of 5 pmol/microL.

Templates and sequencing primers were shipped to the Iowa State University DNA Sequencing Facility at Ames, Iowa for sequencing using standard chemistries for cycle sequencing. In some cases, regions of the template that sequenced poorly using the standard protocols and dye terminators were repeated with the addition of 2 microL DMSO and by using nucleotides optimized for the sequencing of high GC content DNA.

Sequencing data from primer walking and subclones were assembled together to verify that all SL-3 regions had been sequenced from both strands. An open reading frame (ORF) was found in the 9 kilobase Bam H1 fragment, C-terminal of E1 (U.S. Pat. No. 5,536,655), termed Gux1. An ORF of 3366 bp [SEQ ID NO: 2] and deduced amino acid sequence [SEQ ID NO: 1] are shown in Tables 1 and 2. The amino acid sequence predicted by SEQ ID NO: 1 was determined to have significant homology to known cellulases, as is shown below in Example 2 and Table 3.

The amino acid sequence represents a novel member of the family of proteins with cellulase activity. Due to the source of isolation, from the thermophilic *Acidothermus cellulolyticus*, Gux1 is a novel member of cellulases with properties including thermal tolerance. It is also known that thermal tolerant enzymes may have other properties (see definition above).

Example 2

Gux1 Includes a GH48 Catalytic Domain

Sequence alignments and comparisons of the amino acid sequences of the *Acidothermus cellulolyticus* Gux1 catalytic domain (approximately amino acids 231 to 870), *Cellulomonas fimi* (cellobiohydrolase B) and *Thermobifida fusca* (exocellulase E6) polypeptides were prepared, using the ClustalW program (Thompson J. D et al. (1994), Nucleic Acids Res. 22:4673-4680 from EMBL European Bioinformatics Institute website (http://www.ebi.ac.uk/)). An examination of the amino acid sequence alignment of the GH48 domains indicates that the amino acid sequence of Gux1 catalytic domain is homologous to the amino acid sequences of known GH48 family catalytic domains for *C. fimi* cellobiohydrolase B and *T. fusca* exocellulase E6 (see Table 3). In Table 3, the notations are as follows: an asterisk "*" indicates identical or conserved residues in all sequences in the alignment; a colon ":" indicates conserved substitutions; a period "." indicates semi-conserved substitutions; and a hyphen "-" indicates a gap in the sequence. The amino acid sequence predicted for the Gux 1 GH48 domain is approximately 64% identical to the *C. fimi* cellobiohydrolase B GH48 domain and approximately 57% identical to the *T. fusca* exocellulase E6 GH48 domain, indicating that the Gux1 catalytic domain is a member of the GH48 family (Henrissat et al., (1991) supra).

TABLE 3

Multiple amino acid sequence alignment of a Gux1 first catalytic domain and polypeptides with Glycoside Hydrolase Family 48 catalytic domains.

```
Multialignment of related Glycoside Hydrolase Family 48 catalytic domain
GH48_Ace: Acidothermus cellulolyticus Gux1 catalytic domain GH48
GuxB_Cfi: Cellulomonas fimi CBHB(beta-1,4-exocellobiohydrolase). GeneBank
Acc. #AAB00822
E6_Tfu: Thermobifida fusca E6 (beta-1,4-exocellulase). GeneBank Acc.
#AF144563

GH48_Ace  PYIQRFLTMYNKIHDPANGYFSPQG---IPYHSVETLIVEAPDYGHETTSEAYSFWLWLEATY
          (SEQ ID NO:9)
GuxB_Cfi  EYAQRFLAQYDKIKDPANGYFSAQG---IPYHAVETLMVEAPDYGHETTSEAYSYWLWLEALY
          (SEQ ID NO:10)
EG_Tfu    SYDQAFLEQYEKIKDPASGYFREFNGLLVPYHSVETMIVEAPDHGHQTTSEAFSYYLWLEAYY
          * * **  *:**:***.***       :***:***::*****:**:*****:*:.:***** *
          (SEQ ID NO:11)

GH48_Ace  GAVTGNWTPFNNAWTTMETYMIPQHADQPNNASYNPNSPASYAPEEPLPSMYPVAIDSSV
GuxB_Cfi  GQVTQDWAPLNHAWDTMEKYMIPQSVDQPTNSFYNPNSPATYAPEFNHPSSYPSQLNSGI
E6_Tfu    GRVTGDWKPLHDAWESMETFIIPGTKDQPTNSAYNPNSPATYIPEQPNADGYPSPLMNNV
          * **  :*  *:::** :**.::**    ***.*: *******:* **   .. **   :  ...:

GH48_Ace  PVGHDPLAAELQSTYGTPDIYGMHWLADVDNIYGYGDSPGGGCELGPSAKGVSYINTFQR
GuxB_Cfi  SGGTDPIGAELKATYGNADVYQMHWLADVDNIYGFGATPGAGCTLGPTATGTSFINTFQR
E6_Tfu    PVGQDPLAQELSSTYGTNEIYGMHWLLDVDNVYGFGFCGDG------TDDAPAYINTYQR
          . *  **:.  **.:***.  ::* **** ****:**:*     ..       :   . .:***:**

GH48_Ace  GSQESVWETVTQPTCDNGKYGGAHGYVDLFIQG-STPPQWKYTDAPDADARAVQAAYWAY
GuxB_Cfi  GPQESVWETVPQPSCEEFKYGGKNGYLDLFTKDASYAKQWKYTSASDADARAVEAVYWAN
E6_Tfu    GARESVWETIPHPSCDDFTHGGPNGYLDLFTDDQNYAKQWRYTNAPDADARAVQVMFWAH
          * :******::.*:*:: .:**  :**:****     .   ** :** . ********:.  :**

GH48_Ace  TWASAQGKASAIAPTIAKASQTGDYLRYSLFDKYFKQVGNCYPASSCPGATGRQSETYLI
GuxB_Cfi  QWATEQGKAADVAATVAKAAKMGDYLRYTLFDKYFKKIG--CTSPTCAAGQGREAAHYLL
E6_Tfu    EWAKEQGKENEIAGLMDKASKMGDYLRYAMFDKYFKKIGNCVGATSCPGGQGKDSAHYLL
          .**.***  :*  : **:.:  ******::******:.*   :.:*....*:::  **:

GH48_Ace  GWYYAWGGS---SQGWAWRIGDGAAHFGYQNPLAAWAMSNVTPLIPLSPTAKSDWAASLQ
GuxB_Cfi  SWYMAWGGATDTSSGWAWRIGSSHAHFGYQNPLAAWALSTDPKLTPKSPTAKADWAASMQ
E6_Tfu    SWYYSWGGSLDTSSAWAWRIGSSSSHQGYQNVLAAYALSQVPELQPDSPTGVQDWATSFD
          .**  ***:    * .******...  :*  **** ***.:*  . *  ***   ****:*::

GH48_Ace  RQLEFYQWLQSAEGAIAGGATNSWNGNYGTPPAGDSTFYGMAYDWEPVYHDPPSNNWFGF
GuxB_Cfi  RQLEFYTWLQSANGGIAGGATNSWDGAYAQPPAGTPTFYGMGYTEAPVYVDPPSNRWFGM
E6_Tfu    RQLEFLQWLQSAEGGIAGGATNSWKGSYDTPPTGLSQFYGMYYDWQPVWNDPPSNNWFGF
          *****  ***:..:*.*********.*   **:* .  ****    * **: ***** .***.***:

GH48_Ace  QAWSMERVAEYYYVTGDPKAKALLDKWVAWVKPNVTTG-----ASWSIPSNLSWSGQPDT
GuxB_Cfi  QAWGVQRVAELYYASGNAQAKKILDKWVPWVVANISTDG----ASWKVPSELKWTGKPDT
E6_Tfu    QVWNMERVAQLYYVTGDARAEAILDKWVPWAIQHTDVDADNGGQNFQVPSDLEWSGQPDT
          *.*. ::***: ** :*:..*:  :*****.*.   :  ..   .  .: **:*.*:*:***

GH48_Ace  WNPSNPGTNANLHVTITSSGQDVGVAAALAKTLEYYAAKSGDTASRDLAKGLLDSMWNND
GuxB_Cfi  WNAAAPTGNPGLTVEVTSYGQDVGVAADTARALLFYAAKSGDTASRDKAKALLDAIWANN
E6_Tfu    WTG-TYTGNPNLHVQVVSYSQDVGVTAALAKTLMYYAKRSGDTTALATAEGLLDALLAHR
          *.    *..* *  * ::* ******:***:*  *::*  ****::     *** ::   :

GH48_Ace  QDSLGVSTPETRTDYSRFTQVYDPTTGDGLYIPSGWTGTMPNGDQIKPGATFLSIRSWYT
GuxB_Cfi  QDPLGVSAVETRGDYKRFDDTYVAN-GDGIYIPSGWTGTMPNGDVIKPGVSFLDIRSFYR
E6_Tfu    -DSIGIATPEQ-PSWDRLDDPWDGS--EGLYVPPGWSGTMPNGDRIEPGATFLSIRSFYK
          *.:*:::  *    .:.*:  : :  .   :*:*:*.**:*******  *:**.:**.***:*.

GH48_Ace  KDPQWSKVQAYLNGG---PAPTFNYHRFWAESDFAMANADFGMLFPSGSP
GuxB_Cfi  KDPNWSKVQTFLDGG---AEPQFRYHRFWAQTAVAGALADYARLFDDGTT
E6_Tfu    NDPLWPQVEAHLNDPQNVPAPIVERHRFWAQVEIATAFAAHDELFGAGAP
          :**  *.::*  .*..   . * ..*****:  .* * *  ** .*::.
```

Example 3

Mixed Domain GH48, CBD II, CBD III Genes and Hybrid Polypeptides

From the putative locations of the domains in the Gux1 cellulase sequence given above and in comparable cloned cellulase sequences from other species, one can separate individual domains and combine them with one or more domains from different sequences. The significant similarity between cellulase genes permit one by recombinant techniques to arrange one or more domains from the *Acidothermus cellulolyticus* Gux1 cellulase gene with one or more domains from a cellulase gene from one or more other microorganisms. Other representative endoglucanase genes include *Bacillus polymyxa* beta-(1,4) endoglucanase (Baird et al, Journal of Bacteriology, 172: 1576-86 (1992)) and *Xanthomonas campestris* beta-(1,4)-endoglucanase A (Gough et al, Gene 89:53-59 (1990)). The result of the fusion of any two or more domains will, upon expression, be a hybrid polypeptide. Such hybrid polypeptides can have one or more catalytic or binding domains. For ease of manipulation, recombinant techniques may be employed such as the addition of restriction enzyme sites by site-specific mutagenesis. If one is not using one domain of a particular gene, any number of any type of change including complete deletion may be made in the unused domain for convenience of manipulation.

It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to references such as patents, patent applications, and publications. Each is hereby incorporated by reference for all purposes.

---

We claim:

1. A composition comprising an isolated protein with catalytic activity of an exoglucanase, said protein comprising a glycoside hydrolase 48 (GH48) catalytic domain of SEQ ID NO:5, a carbohydrate binding domain (CBD) type III of SEQ ID NO:4 and possessing carbohydrate binding activity, and a carbohydrate binding domain (CBD) type II of SEQ ID NO:7 and possessing carbohydrate binding activity.

2. The composition of claim 1 wherein the protein is further defined as comprising a linker and a signal peptide.

3. An isolated protein with catalytic activity of an exoglucanase having the sequence of SEQ ID NO: 1.

4. The protein of claim 3 further defined as being encoded by a polynucleotide having the sequence of SEQ ID NO: 2.

5. The composition of claim 1 wherein the protein further comprises a linker of SEQ ID NO: 6.

6. The composition of claim 1, wherein the protein further comprises a peptide tag.

7. The composition of claim 6 wherein the peptide tag is 6-His (SEQ ID NO: 8), thioredoxin, hemaglutinin, GST, or OmpA signal sequence tag.

8. The composition of claim 1 wherein the protein further comprises a substrate targeting moiety.

9. The composition of claim 1 further comprising a carrier.

10. The composition of claim 1 wherein the protein is further defined as comprising a heterologous peptide or protein.

11. The composition of claim 10 wherein the heterologous peptide or protein comprises an immunoglobulin.

12. The composition of claim 10 wherein the heterologous peptide comprises a histidine tag.

13. The composition of claim 10 wherein the heterologous peptide comprises a leucine zipper.

14. The composition of claim 1 further defined as comprising, in combination, the sequence of SEQ ID NO: 4, SEQ ID NO: 5, and SEQ ID NO: 7 in that particular order.

15. The composition of claim 10 wherein the heterologous peptide comprises a fusion protein.

16. The composition of claim 15, wherein the heterologous peptide is a substrate targeting moiety.

17. The composition of claim 15, wherein the heterologous peptide is a peptide tag.

18. The composition of claim 17, wherein the peptide tag is 6-His (SEQ ID NO:8), thioredoxin, hemaglutinin, GST, or OmpA signal sequence tag.

19. The composition of claim 15, wherein the heterologous peptide is an agent that promotes polypeptide oligomerization.

\* \* \* \* \*

SEQUENCE LISTING

```
<160> NUMBER OF SEQ ID NOS: 11

<210> SEQ ID NO 1
<211> LENGTH: 1121
<212> TYPE: PRT
<213> ORGANISM: Acidothermus cellulolyticus
<220> FEATURE:
<221> NAME/KEY: misc_feature
<223> OTHER INFORMATION: Full-length sequence of Gux1 protein

<400> SEQUENCE: 1

Met Pro Gly Leu Arg Arg Arg Leu Arg Ala Gly Ile Val Ser Ala Ala
1               5                   10                  15

Ala Leu Gly Ser Leu Val Ser Gly Leu Val Ala Val Ala Pro Val Ala
                20                  25                  30

His Ala Ala Val Thr Leu Lys Ala Gln Tyr Lys Asn Asn Asp Ser Ala
            35                  40                  45

Pro Ser Asp Asn Gln Ile Lys Pro Gly Leu Gln Leu Val Asn Thr Gly
        50                  55                  60

Ser Ser Ser Val Asp Leu Ser Thr Val Thr Val Arg Tyr Trp Phe Thr
65                  70                  75                  80

Arg Asp Gly Gly Ser Ser Thr Leu Val Tyr Asn Cys Asp Trp Ala Ala
                85                  90                  95

Met Gly Cys Gly Asn Ile Arg Ala Ser Phe Gly Ser Val Asn Pro Ala
                100                 105                 110

Thr Pro Thr Ala Asp Thr Tyr Leu Gln Leu Ser Phe Thr Gly Gly Thr
            115                 120                 125

Leu Ala Ala Gly Gly Ser Thr Gly Glu Ile Gln Asn Arg Val Asn Lys
        130                 135                 140

Ser Asp Trp Ser Asn Phe Asp Glu Thr Asn Asp Tyr Ser Tyr Gly Thr
145                 150                 155                 160

Asn Thr Thr Phe Gln Asp Trp Thr Lys Val Thr Val Tyr Val Asn Gly
                165                 170                 175

Val Leu Val Trp Gly Thr Glu Pro Ser Gly Ala Thr Ala Ser Pro Ser
                180                 185                 190

Ala Ser Ala Thr Pro Ser Pro Ser Ser Pro Thr Thr Ser Pro Ser
            195                 200                 205
```

```
Ser Ser Pro Ser Pro Ser Ser Pro Thr Pro Thr Pro Ser Ser Ser
    210                 215                 220

Ser Pro Pro Ser Ser Asn Asp Pro Tyr Ile Gln Arg Phe Leu Thr
225                 230                 235                 240

Met Tyr Asn Lys Ile His Asp Pro Ala Asn Gly Tyr Phe Ser Pro Gln
            245                 250                 255

Gly Ile Pro Tyr His Ser Val Glu Thr Leu Ile Val Glu Ala Pro Asp
            260                 265                 270

Tyr Gly His Glu Thr Thr Ser Glu Ala Tyr Ser Phe Trp Leu Trp Leu
        275                 280                 285

Glu Ala Thr Tyr Gly Ala Val Thr Gly Asn Trp Thr Pro Phe Asn Asn
    290                 295                 300

Ala Trp Thr Thr Met Glu Thr Tyr Met Ile Pro Gln His Ala Asp Gln
305                 310                 315                 320

Pro Asn Asn Ala Ser Tyr Asn Pro Asn Ser Pro Ala Ser Tyr Ala Pro
                325                 330                 335

Glu Glu Pro Leu Pro Ser Met Tyr Pro Val Ala Ile Asp Ser Ser Val
            340                 345                 350

Pro Val Gly His Asp Pro Leu Ala Ala Glu Leu Gln Ser Thr Tyr Gly
        355                 360                 365

Thr Pro Asp Ile Tyr Gly Met His Trp Leu Ala Asp Val Asp Asn Ile
    370                 375                 380

Tyr Gly Tyr Gly Asp Ser Pro Gly Gly Gly Cys Glu Leu Gly Pro Ser
385                 390                 395                 400

Ala Lys Gly Val Ser Tyr Ile Asn Thr Phe Gln Arg Gly Ser Gln Glu
                405                 410                 415

Ser Val Trp Glu Thr Val Thr Gln Pro Thr Cys Asp Asn Gly Lys Tyr
            420                 425                 430

Gly Gly Ala His Gly Tyr Val Asp Leu Phe Ile Gln Gly Ser Thr Pro
        435                 440                 445

Pro Gln Trp Lys Tyr Thr Asp Ala Pro Asp Ala Asp Ala Arg Ala Val
    450                 455                 460

Gln Ala Ala Tyr Trp Ala Tyr Thr Trp Ala Ser Ala Gln Gly Lys Ala
465                 470                 475                 480

Ser Ala Ile Ala Pro Thr Ile Ala Lys Ala Ser Gln Thr Gly Asp Tyr
                485                 490                 495

Leu Arg Tyr Ser Leu Phe Asp Lys Tyr Phe Lys Gln Val Gly Asn Cys
            500                 505                 510

Tyr Pro Ala Ser Ser Cys Pro Ala Thr Gly Arg Gln Ser Glu Thr
        515                 520                 525

Tyr Leu Ile Gly Trp Tyr Tyr Ala Trp Gly Gly Ser Ser Gln Gly Trp
    530                 535                 540

Ala Trp Arg Ile Gly Asp Gly Ala Ala His Phe Gly Tyr Gln Asn Pro
545                 550                 555                 560

Leu Ala Ala Trp Ala Met Ser Asn Val Thr Pro Leu Ile Pro Leu Ser
                565                 570                 575

Pro Thr Ala Lys Ser Asp Trp Ala Ser Leu Gln Arg Gln Leu Glu
            580                 585                 590

Phe Tyr Gln Trp Leu Gln Ser Ala Glu Gly Ala Ile Ala Gly Gly Ala
        595                 600                 605

Thr Asn Ser Trp Asn Gly Asn Tyr Gly Thr Pro Pro Ala Gly Asp Ser
    610                 615                 620

Thr Phe Tyr Gly Met Ala Tyr Asp Trp Glu Pro Val Tyr His Asp Pro
```

-continued

```
                625                 630                 635                 640
Pro Ser Asn Asn Trp Phe Gly Phe Gln Ala Trp Ser Met Glu Arg Val
                    645                 650                 655
Ala Glu Tyr Tyr Tyr Val Thr Gly Asp Pro Lys Ala Lys Ala Leu Leu
                    660                 665                 670
Asp Lys Trp Val Ala Val Lys Pro Asn Val Thr Thr Gly Ala Ser
                    675                 680                 685
Trp Ser Ile Pro Ser Asn Leu Ser Trp Ser Gly Gln Pro Asp Thr Trp
                    690                 695                 700
Asn Pro Ser Asn Pro Gly Thr Asn Ala Asn Leu His Val Thr Ile Thr
705                 710                 715                 720
Ser Ser Gly Gln Asp Val Gly Val Ala Ala Leu Ala Lys Thr Leu
                    725                 730                 735
Glu Tyr Tyr Ala Ala Lys Ser Gly Asp Thr Ala Ser Arg Asp Leu Ala
                    740                 745                 750
Lys Gly Leu Leu Asp Ser Met Trp Asn Asn Gln Asp Ser Leu Gly
                    755                 760                 765
Val Ser Thr Pro Glu Thr Arg Thr Asp Tyr Ser Arg Phe Thr Gln Val
770                 775                 780
Tyr Asp Pro Thr Thr Gly Asp Gly Leu Tyr Ile Pro Ser Gly Trp Thr
785                 790                 795                 800
Gly Thr Met Pro Asn Gly Asp Gln Ile Lys Pro Gly Ala Thr Phe Leu
                    805                 810                 815
Ser Ile Arg Ser Trp Tyr Thr Lys Asp Pro Gln Trp Ser Lys Val Gln
                    820                 825                 830
Ala Tyr Leu Asn Gly Gly Pro Ala Pro Thr Phe Asn Tyr His Arg Phe
                    835                 840                 845
Trp Ala Glu Ser Asp Phe Ala Met Ala Asn Ala Asp Phe Gly Met Leu
                    850                 855                 860
Phe Pro Ser Gly Ser Pro Ser Pro Thr Pro Ser Pro Thr Pro Thr Ser
865                 870                 875                 880
Ser Pro Ser Pro Thr Pro Ser Ser Pro Thr Pro Ser Pro Ser Pro
                    885                 890                 895
Ser Pro Thr Gly Asp Thr Thr Pro Pro Ser Val Pro Thr Gly Leu Gln
                    900                 905                 910
Val Thr Gly Thr Thr Thr Ser Ser Val Ser Leu Ser Trp Thr Ala Ser
                    915                 920                 925
Thr Asp Asn Val Gly Val Ala His Tyr Asn Val Tyr Arg Asn Gly Thr
                    930                 935                 940
Leu Val Gly Gln Pro Thr Ala Thr Ser Phe Thr Asp Thr Gly Leu Ala
945                 950                 955                 960
Ala Gly Thr Ser Tyr Thr Tyr Thr Val Ala Ala Val Asp Ala Ala Gly
                    965                 970                 975
Asn Thr Ser Ala Gln Ser Phe Ala Gly Asp Ser Asp Gly Ile Ala
                    980                 985                 990
Val Ala Ser Pro Ser Pro Ser Pro  Thr Pro Thr Ser Ser  Pro Ser Pro
                    995                 1000                1005
Thr Pro  Ser Pro Thr Pro Ser  Pro Thr Ser Thr  Gly Ala Ser
     1010               1015                1020
Cys Thr  Ala Thr Tyr Val Val  Asn Ser Asp Trp  Ser Gly Phe
     1025               1030                1035
Thr Thr  Thr Val Thr Val Thr  Asn Thr Gly Thr Arg  Ala Thr Ser
     1040               1045                1050
```

```
Gly Trp Thr Val Thr Trp Ser Phe Ala Gly Asn Gln Thr Val Thr
    1055                1060                1065

Asn Tyr Trp Asn Thr Ala Leu Thr Gln Ser Gly Lys Ser Val Thr
    1070                1075                1080

Ala Lys Asn Leu Ser Tyr Asn Asn Val Ile Gln Pro Gly Gln Ser
    1085                1090                1095

Thr Thr Phe Gly Phe Asn Gly Ser Tyr Ser Gly Thr Asn Thr Ala
    1100                1105                1110

Pro Thr Leu Ser Cys Thr Ala Ser
    1115                1120

<210> SEQ ID NO 2
<211> LENGTH: 3365
<212> TYPE: DNA
<213> ORGANISM: Acidothermus cellulolyticus
<220> FEATURE:
<221> NAME/KEY: misc_feature
<223> OTHER INFORMATION: Gux1 full-length coding sequence

<400> SEQUENCE: 2
atgccaggat tacgacggcg actccgcgcc ggtatcgtct cggcggcggc gttggggtcg      60
ctggttagcg ggctcgttgc cgtcgcacca gtcgcgcacg cggcggtgac tctcaaagcg     120
cagtataaga acaatgattc ggcgccgagt gacaaccaga tcaaaccggg tctccagttg     180
gtgaataccg gtcgtcgtc ggtggatttg tcgacggtga cggtgcggta ctggttcacc     240
cgggatggtg ggtcgtcgac actggtgtac aactgtgact gggcggcgat ggggtgtggg     300
aatatccgcg cctcgttcgg ctcggtgaac ccggcgacgc cgacggcgga cacctacctg     360
cagttgtcgt tcactggtgg aacgttggcc gctggtgggt cgacgggtga gattcaaaac     420
cgggtgaata agagtgactg gtcgaacttt gatgagacca atgactactc gtatgggacg     480
aacaccacct tccaggactg gacgaaggtg acggtgtacg tcaacggcgt gttggtctgg     540
gggaccgaac cgtccggagc gacggcgtct ccatccgcgt cggcgacgcc cagcccgtcc     600
agttcaccga ccacgagtcc gagttcgtcc cgtcgccga gcagcagccc gacgccgaca     660
ccgagcagct cgtcgccgcc ccgtcgtcca acgacccgta catccagcgg ttcctcacga     720
tgtacaacaa gattcacgac ccagcgaacg gctacttcag cccgcaggga attccctacc     780
actcggtaga aacgctcatc gttgaggcac cggactacgg gcacgagaca acttcggagg     840
cgtacagctt ctggctctgg ctcgaagcga cgtacgcgc agtgaccggc aactggacgc     900
cgttcaacaa cgcctggacg acgatggaaa cgtacatgat cccgcagcac gcggaccagc     960
cgaacaacgc gtcgtacaac cccaacagcc cggcgtcgta cgctccggaa gagccgctgc    1020
ccagcatgta cccggttgcc atcgacagca gcgtgccggt tgggcacgac ccgctcgccg    1080
ccgaattgca gtcgacgtac ggcactccgg acatttacgg catgcactgg ctggccgacg    1140
ttgacaacat ctacggatac ggcgacagcc ccggcggtgg ttgcgaactc ggtccttccg    1200
ctaagggcgt ctcctacatc aacacattcc agcgcggctc gcaggagtcc gtctgggaga    1260
cggtcaccca gccgacgtgc gacaacggca agtacgtgg ggcgcacggc tacgtcgacc    1320
tgttcatcca gggttcgacg ccgccgcagt ggaagtacac cgatgccccg gacgccgacg    1380
cccgtgccgt ccaggctgcg tactgggcct acacctgggc atcggcgcag ggcaaggcaa    1440
gcgcgattgc cccgacgatc gccaaggcga gccaaaccgg cgactacctg cggtactcgc    1500
tctttgacaa gtacttcaag caggtcggca actgctaccg ggccagctcc tgccctggag    1560
```

-continued

```
caaccggacg ccagagcgag acctacctga tcggctggta ctacgcctgg ggcggctcaa    1620
gccaaggctg ggcctggcgc attggtgacg cgccgcgca cttcggctac cagaatccgc    1680
ttgccgcgtg ggcgatgtcg aacgtgacac cgctcattcc gctctcgccc acggcaaaga    1740
gcgactgggc ggcgagcttg cagcgccagc tggagttcta ccagtggttg caatccgcgg    1800
aaggagccat tgcgggcggc gccaccaaca gctggaacgg caattacggg accccgccgg    1860
ccggagactc gaccttctac ggcatggcgt acgactggga gccggtctac cacgacccgc    1920
cgagcaacaa ctggttcggc ttccaggcgt ggtccatgga acgggttgcc gagtactact    1980
acgtcaccgg cgacccgaag gccaaggcgc tgctcgacaa gtgggtcgca tgggtgaagc    2040
cgaatgtcac caccggtgcc tcatggtcga ttccgtcgaa tttgtcctgg agcggccaac    2100
cggatacctg gaatccgagc aacccaggaa cgaatgccaa cctgcacgtg accatcacgt    2160
cgtccgggca ggacgtcggt gttgccgcgg cgctcgcgaa gacactcgag tactacgcgg    2220
caaaatccgg cgatacggcc tcgcgcgacc tcgcgaaggg attgctcgac tccatgtgga    2280
acaacgacca ggacagcctc ggtgtgagca caccggagac gcggaccgac tactctcggt    2340
tcactcaggt gtacgacccg acgactggtg acggcctcta catcccgtcg ggttggacgg    2400
ggaccatgcc caacggtgac caaatcaagc cgggtgcgac cttcctgagc atccggtcct    2460
ggtacaccaa ggatccgcag tggtcgaagg tgcaggcgta cctcaacggc gggcctgctc    2520
cgacgttcaa ctaccaccgg ttctgggcgg agtccgactt cgcgatggcg aacgccgatt    2580
ttggcatgct cttcccatcc gggtcgccca gcccgacccc gagcccgact ccgacgtcgt    2640
ccccgagccc gactccgagc agctcgccga cgccgtcgcc cagcccgtca ccgaccggcg    2700
acaccacgcc gccgagcgtg ccgacgggtc ttcaggtcac cgggacaacg acgtcgtccg    2760
tgtcgctcag ctggaccgcg tccaccgaca acgtcggcgt cgcgcactac aacgtgtacc    2820
gaaacggcac gctggtgggt cagccgacag cgacgtcgtt cacggacacc ggcctggctg    2880
ctggcacgtc gtacacgtac acagtggcgg ccgttgatgc ggccggtaac acgtcggcgc    2940
agagcttcgc cggtgacagc gacgacggca tcgccgtcgc gagcccgtcg ccgagcccga    3000
ctccgacgtc gtccccgagc ccaacgccgt cgccgacacc gtcaccgacg tccaccagcg    3060
gcgcatcgtg cactgctacc tacgttgtca atagcgactg gggtagcggc ttcacgacaa    3120
ccgtgaccgt gacgaacacc ggcaccaggg ccaccagtgg ctggacggtc acgtggagct    3180
ttgccggtaa tcagacggtc accaactact ggaacaccgc gctgacgcaa tccggaaagt    3240
cggtgaccgc aaagaacctg agttacaaca acgtcatcca acctggtcag tcgacgacct    3300
ttggattcaa cggaagttac tcaggaacaa acaccgcgcc gacgctcagc tgcacggcaa    3360
gctga                                                                3365
```

```
<210> SEQ ID NO 3
<211> LENGTH: 34
<212> TYPE: PRT
<213> ORGANISM: Acidothermus cellulolyticus
<220> FEATURE:
<221> NAME/KEY: misc_feature
<223> OTHER INFORMATION: Potential signal peptide of Gux1

<400> SEQUENCE: 3

Met Pro Gly Leu Arg Arg Arg Leu Arg Ala Gly Ile Val Ser Ala Ala
1               5                   10                  15

Ala Leu Gly Ser Leu Val Ser Gly Leu Val Ala Val Ala Pro Val Ala
                20                  25                  30
```

His Ala

<210> SEQ ID NO 4
<211> LENGTH: 153
<212> TYPE: PRT
<213> ORGANISM: Acidothermus cellulolyticus
<220> FEATURE:
<221> NAME/KEY: misc_feature
<223> OTHER INFORMATION: CBD III of Gux1

<400> SEQUENCE: 4

```
Ala Val Thr Leu Lys Ala Gln Tyr Lys Asn Asn Asp Ser Ala Pro Ser
1               5                   10                  15

Asp Asn Gln Ile Lys Pro Gly Leu Gln Leu Val Asn Thr Gly Ser Ser
            20                  25                  30

Ser Val Asp Leu Ser Thr Val Thr Val Arg Tyr Trp Phe Thr Arg Asp
        35                  40                  45

Gly Gly Ser Ser Thr Leu Val Tyr Asn Cys Asp Trp Ala Ala Met Gly
    50                  55                  60

Cys Gly Asn Ile Arg Ala Ser Phe Gly Ser Val Asn Pro Ala Thr Pro
65                  70                  75                  80

Thr Ala Asp Thr Tyr Leu Gln Leu Ser Phe Thr Gly Thr Leu Ala
                85                  90                  95

Ala Gly Gly Ser Thr Gly Glu Ile Gln Asn Arg Val Asn Lys Ser Asp
                100                 105                 110

Trp Ser Asn Phe Asp Glu Thr Asn Asp Tyr Ser Tyr Gly Thr Asn Thr
            115                 120                 125

Thr Phe Gln Asp Trp Thr Lys Val Thr Val Tyr Val Asn Gly Val Leu
        130                 135                 140

Val Trp Gly Thr Glu Pro Ser Gly Ala
145                 150
```

<210> SEQ ID NO 5
<211> LENGTH: 640
<212> TYPE: PRT
<213> ORGANISM: Acidothermus cellulolyticus
<220> FEATURE:
<221> NAME/KEY: misc_feature
<223> OTHER INFORMATION: GH48 domain of Gux1

<400> SEQUENCE: 5

```
Asn Asp Pro Tyr Ile Gln Arg Phe Leu Thr Met Tyr Asn Lys Ile His
1               5                   10                  15

Asp Pro Ala Asn Gly Tyr Phe Ser Pro Gln Gly Ile Pro Tyr His Ser
            20                  25                  30

Val Glu Thr Leu Ile Val Glu Ala Pro Asp Tyr Gly His Glu Thr Thr
        35                  40                  45

Ser Glu Ala Tyr Ser Phe Trp Leu Trp Leu Glu Ala Thr Tyr Gly Ala
    50                  55                  60

Val Thr Gly Asn Trp Thr Pro Phe Asn Asn Ala Trp Thr Thr Met Glu
65                  70                  75                  80

Thr Tyr Met Ile Pro Gln His Ala Asp Gln Pro Asn Asn Ala Ser Tyr
                85                  90                  95

Asn Pro Asn Ser Pro Ala Ser Tyr Ala Pro Glu Glu Pro Leu Pro Ser
                100                 105                 110

Met Tyr Pro Val Ala Ile Asp Ser Ser Val Pro Val Gly His Asp Pro
            115                 120                 125

Leu Ala Ala Glu Leu Gln Ser Thr Tyr Gly Thr Pro Asp Ile Tyr Gly
```

```
            130                 135                 140
Met His Trp Leu Ala Asp Val Asp Asn Ile Tyr Gly Tyr Gly Asp Ser
145                 150                 155                 160

Pro Gly Gly Gly Cys Glu Leu Gly Pro Ser Ala Lys Gly Val Ser Tyr
                165                 170                 175

Ile Asn Thr Phe Gln Arg Gly Ser Gln Glu Ser Val Trp Glu Thr Val
            180                 185                 190

Thr Gln Pro Thr Cys Asp Asn Gly Lys Tyr Gly Gly Ala His Gly Tyr
        195                 200                 205

Val Asp Leu Phe Ile Gln Gly Ser Thr Pro Pro Gln Trp Lys Tyr Thr
210                 215                 220

Asp Ala Pro Asp Ala Asp Ala Arg Ala Val Gln Ala Ala Tyr Trp Ala
225                 230                 235                 240

Tyr Thr Trp Ala Ser Ala Gln Gly Lys Ala Ser Ala Ile Ala Pro Thr
                245                 250                 255

Ile Ala Lys Ala Ser Gln Thr Gly Asp Tyr Leu Arg Tyr Ser Leu Phe
            260                 265                 270

Asp Lys Tyr Phe Lys Gln Val Gly Asn Cys Tyr Pro Ala Ser Ser Cys
        275                 280                 285

Pro Gly Ala Thr Gly Arg Gln Ser Glu Thr Tyr Leu Ile Gly Trp Tyr
    290                 295                 300

Tyr Ala Trp Gly Gly Ser Ser Gln Gly Trp Ala Trp Arg Ile Gly Asp
305                 310                 315                 320

Gly Ala Ala His Phe Gly Tyr Gln Asn Pro Leu Ala Ala Trp Ala Met
                325                 330                 335

Ser Asn Val Thr Pro Leu Ile Pro Leu Ser Pro Thr Ala Lys Ser Asp
            340                 345                 350

Trp Ala Ala Ser Leu Gln Arg Gln Leu Glu Phe Tyr Gln Trp Leu Gln
        355                 360                 365

Ser Ala Glu Gly Ala Ile Ala Gly Gly Ala Thr Asn Ser Trp Asn Gly
    370                 375                 380

Asn Tyr Gly Thr Pro Pro Ala Gly Asp Ser Thr Phe Tyr Gly Met Ala
385                 390                 395                 400

Tyr Asp Trp Glu Pro Val Tyr His Asp Pro Pro Ser Asn Asn Trp Phe
                405                 410                 415

Gly Phe Gln Ala Trp Ser Met Glu Arg Val Ala Glu Tyr Tyr Tyr Val
            420                 425                 430

Thr Gly Asp Pro Lys Ala Lys Ala Leu Leu Asp Lys Trp Val Ala Trp
        435                 440                 445

Val Lys Pro Asn Val Thr Thr Gly Ala Ser Trp Ser Ile Pro Ser Asn
450                 455                 460

Leu Ser Trp Ser Gly Gln Pro Asp Thr Trp Asn Pro Ser Asn Pro Gly
465                 470                 475                 480

Thr Asn Ala Asn Leu His Val Thr Ile Thr Ser Ser Gly Gln Asp Val
                485                 490                 495

Gly Val Ala Ala Ala Leu Ala Lys Thr Leu Glu Tyr Tyr Ala Ala Lys
            500                 505                 510

Ser Gly Asp Thr Ala Ser Arg Asp Leu Ala Lys Gly Leu Leu Asp Ser
        515                 520                 525

Met Trp Asn Asn Asp Gln Asp Ser Leu Gly Val Ser Thr Pro Glu Thr
    530                 535                 540

Arg Thr Asp Tyr Ser Arg Phe Thr Gln Val Tyr Asp Pro Thr Thr Gly
545                 550                 555                 560
```

```
Asp Gly Leu Tyr Ile Pro Ser Gly Trp Thr Gly Thr Met Pro Asn Gly
                565                 570                 575

Asp Gln Ile Lys Pro Gly Ala Thr Phe Leu Ser Ile Arg Ser Trp Tyr
            580                 585                 590

Thr Lys Asp Pro Gln Trp Ser Lys Val Gln Ala Tyr Leu Asn Gly Gly
        595                 600                 605

Pro Ala Pro Thr Phe Asn Tyr His Arg Phe Trp Ala Glu Ser Asp Phe
    610                 615                 620

Ala Met Ala Asn Ala Asp Phe Gly Met Leu Phe Pro Ser Gly Ser Pro
625                 630                 635                 640

<210> SEQ ID NO 6
<211> LENGTH: 85
<212> TYPE: PRT
<213> ORGANISM: Acidothermus cellulolyticus
<220> FEATURE:
<221> NAME/KEY: misc_feature
<223> OTHER INFORMATION: FN III domain of Gux1

<400> SEQUENCE: 6

Asp Thr Thr Pro Pro Ser Val Pro Thr Gly Leu Gln Val Thr Gly Thr
1               5                   10                  15

Thr Thr Ser Ser Val Ser Leu Ser Trp Thr Ala Ser Thr Asp Asn Val
            20                  25                  30

Gly Val Ala His Tyr Asn Val Tyr Arg Asn Gly Thr Leu Val Gly Gln
        35                  40                  45

Pro Thr Ala Thr Ser Phe Thr Asp Thr Gly Leu Ala Ala Gly Thr Ser
    50                  55                  60

Tyr Thr Tyr Thr Val Ala Ala Val Asp Ala Ala Gly Asn Thr Ser Ala
65                  70                  75                  80

Gln Ser Phe Ala Gly
                85

<210> SEQ ID NO 7
<211> LENGTH: 101
<212> TYPE: PRT
<213> ORGANISM: Acidothermus cellulolyticus
<220> FEATURE:
<221> NAME/KEY: misc_feature
<223> OTHER INFORMATION: CBD II domain of Gux1

<400> SEQUENCE: 7

Gly Ala Ser Cys Thr Ala Thr Tyr Val Val Asn Ser Asp Trp Gly Ser
1               5                   10                  15

Gly Phe Thr Thr Thr Val Thr Val Thr Asn Thr Gly Thr Arg Ala Thr
            20                  25                  30

Ser Gly Trp Thr Val Thr Trp Ser Phe Ala Gly Asn Gln Thr Val Thr
        35                  40                  45

Asn Tyr Trp Asn Thr Ala Leu Thr Gln Ser Gly Lys Ser Val Thr Ala
    50                  55                  60

Lys Asn Leu Ser Tyr Asn Asn Val Ile Gln Pro Gly Gln Ser Thr Thr
65                  70                  75                  80

Phe Gly Phe Asn Gly Ser Tyr Ser Gly Thr Asn Thr Ala Pro Thr Leu
                85                  90                  95

Ser Cys Thr Ala Ser
            100

<210> SEQ ID NO 8
```

```
<211> LENGTH: 6
<212> TYPE: PRT
<213> ORGANISM: Artificial
<220> FEATURE:
<223> OTHER INFORMATION: Synthetic histidine tag
<220> FEATURE:
<221> NAME/KEY: misc_feature
<223> OTHER INFORMATION: Synthetic His Tag

<400> SEQUENCE: 8

His His His His His His
1               5

<210> SEQ ID NO 9
<211> LENGTH: 638
<212> TYPE: PRT
<213> ORGANISM: Acidothermus cellulolyticus
<220> FEATURE:
<221> NAME/KEY: misc_feature
<223> OTHER INFORMATION: GH48 domain of Acdothermus cellulolyticus

<400> SEQUENCE: 9

Pro Tyr Ile Gln Arg Phe Leu Thr Met Tyr Asn Lys Ile His Asp Pro
1               5                   10                  15

Ala Asn Gly Tyr Phe Ser Pro Gln Gly Ile Pro Tyr His Ser Val Glu
            20                  25                  30

Thr Leu Ile Val Glu Ala Pro Asp Tyr Gly His Glu Thr Thr Ser Glu
        35                  40                  45

Ala Tyr Ser Phe Trp Leu Trp Leu Glu Ala Thr Tyr Gly Ala Val Thr
    50                  55                  60

Gly Asn Trp Thr Pro Phe Asn Asn Ala Trp Thr Thr Met Glu Thr Tyr
65                  70                  75                  80

Met Ile Pro Gln His Ala Asp Gln Pro Asn Asn Ala Ser Tyr Asn Pro
                85                  90                  95

Asn Ser Pro Ala Ser Tyr Ala Pro Glu Glu Pro Leu Pro Ser Met Tyr
            100                 105                 110

Pro Val Ala Ile Asp Ser Ser Val Pro Val Gly His Asp Pro Leu Ala
        115                 120                 125

Ala Glu Leu Gln Ser Thr Tyr Gly Thr Pro Asp Ile Tyr Gly Met His
    130                 135                 140

Trp Leu Ala Asp Val Asp Asn Ile Tyr Gly Tyr Gly Asp Ser Pro Gly
145                 150                 155                 160

Gly Gly Cys Glu Leu Gly Pro Ser Ala Lys Gly Val Ser Tyr Ile Asn
                165                 170                 175

Thr Phe Gln Arg Gly Ser Gln Glu Ser Val Trp Glu Thr Val Thr Gln
            180                 185                 190

Pro Thr Cys Asp Asn Gly Lys Tyr Gly Gly Ala His Gly Tyr Val Asp
        195                 200                 205

Leu Phe Ile Gln Gly Ser Thr Pro Gln Trp Lys Tyr Thr Asp Ala
    210                 215                 220

Pro Asp Ala Asp Ala Arg Ala Val Gln Ala Ala Tyr Trp Ala Tyr Thr
225                 230                 235                 240

Trp Ala Ser Ala Gln Gly Lys Ala Ser Ala Ile Ala Pro Thr Ile Ala
                245                 250                 255

Lys Ala Ser Gln Thr Gly Asp Tyr Leu Arg Tyr Ser Leu Phe Asp Lys
            260                 265                 270

Tyr Phe Lys Gln Val Gly Asn Cys Tyr Pro Ala Ser Ser Cys Pro Gly
        275                 280                 285
```

```
Ala Thr Gly Arg Gln Ser Glu Thr Tyr Leu Ile Gly Trp Tyr Tyr Ala
    290                 295                 300

Trp Gly Gly Ser Ser Gln Gly Trp Ala Trp Arg Ile Gly Asp Gly Ala
305                 310                 315                 320

Ala His Phe Gly Tyr Gln Asn Pro Leu Ala Ala Trp Ala Met Ser Asn
                325                 330                 335

Val Thr Pro Leu Ile Pro Leu Ser Pro Thr Ala Lys Ser Asp Trp Ala
            340                 345                 350

Ala Ser Leu Gln Arg Gln Leu Glu Phe Tyr Gln Trp Leu Gln Ser Ala
        355                 360                 365

Glu Gly Ala Ile Ala Gly Gly Ala Thr Asn Ser Trp Asn Gly Asn Tyr
    370                 375                 380

Gly Thr Pro Pro Ala Gly Asp Ser Thr Phe Tyr Gly Met Ala Tyr Asp
385                 390                 395                 400

Trp Glu Pro Val Tyr His Asp Pro Pro Ser Asn Asn Trp Phe Gly Phe
                405                 410                 415

Gln Ala Trp Ser Met Glu Arg Val Ala Glu Tyr Tyr Val Thr Gly
            420                 425                 430

Asp Pro Lys Ala Lys Ala Leu Leu Asp Lys Trp Val Ala Trp Val Lys
        435                 440                 445

Pro Asn Val Thr Thr Gly Ala Ser Trp Ser Ile Pro Ser Asn Leu Ser
    450                 455                 460

Trp Ser Gly Gln Pro Asp Thr Trp Asn Pro Ser Asn Pro Gly Thr Asn
465                 470                 475                 480

Ala Asn Leu His Val Thr Ile Thr Ser Ser Gly Gln Asp Val Gly Val
                485                 490                 495

Ala Ala Ala Leu Ala Lys Thr Leu Glu Tyr Tyr Ala Ala Lys Ser Gly
            500                 505                 510

Asp Thr Ala Ser Arg Asp Leu Ala Lys Gly Leu Leu Asp Ser Met Trp
        515                 520                 525

Asn Asn Asp Gln Asp Ser Leu Gly Val Ser Thr Pro Glu Thr Arg Thr
    530                 535                 540

Asp Tyr Ser Arg Phe Thr Gln Val Tyr Asp Pro Thr Thr Gly Asp Gly
545                 550                 555                 560

Leu Tyr Ile Pro Ser Gly Trp Thr Gly Thr Met Pro Asn Gly Asp Gln
                565                 570                 575

Ile Lys Pro Gly Ala Thr Phe Leu Ser Ile Arg Ser Trp Tyr Thr Lys
            580                 585                 590

Asp Pro Gln Trp Ser Lys Val Gln Ala Tyr Leu Asn Gly Gly Pro Ala
        595                 600                 605

Pro Thr Phe Asn Tyr His Arg Phe Trp Ala Glu Ser Asp Phe Ala Met
    610                 615                 620

Ala Asn Ala Asp Phe Gly Met Leu Phe Pro Ser Gly Ser Pro
625                 630                 635

<210> SEQ ID NO 10
<211> LENGTH: 640
<212> TYPE: PRT
<213> ORGANISM: Cellulomonas fimi
<220> FEATURE:
<221> NAME/KEY: misc_feature
<223> OTHER INFORMATION: Cellulomonas fimi CBHB

<400> SEQUENCE: 10

Glu Tyr Ala Gln Arg Phe Leu Ala Gln Tyr Asp Lys Ile Lys Asp Pro
1               5                   10                  15
```

```
Ala Asn Gly Tyr Phe Ser Ala Gln Gly Ile Pro Tyr His Ala Val Glu
                20                  25                  30

Thr Leu Met Val Glu Ala Pro Asp Tyr Gly His Glu Thr Thr Ser Glu
            35                  40                  45

Ala Tyr Ser Tyr Trp Leu Trp Leu Glu Ala Leu Tyr Gly Gln Val Thr
        50                  55                  60

Gln Asp Trp Ala Pro Leu Asn His Ala Trp Asp Thr Met Glu Lys Tyr
65                  70                  75                  80

Met Ile Pro Gln Ser Val Asp Gln Pro Thr Asn Ser Phe Tyr Asn Pro
                85                  90                  95

Asn Ser Pro Ala Thr Tyr Ala Pro Glu Phe Asn His Pro Ser Ser Tyr
            100                 105                 110

Pro Ser Gln Leu Asn Ser Gly Ile Ser Gly Gly Thr Asp Pro Ile Gly
        115                 120                 125

Ala Glu Leu Lys Ala Thr Tyr Gly Asn Ala Asp Val Tyr Gln Met His
    130                 135                 140

Trp Leu Ala Asp Val Asp Asn Ile Tyr Gly Phe Gly Ala Thr Pro Gly
145                 150                 155                 160

Ala Gly Cys Thr Leu Gly Pro Thr Ala Thr Gly Thr Ser Phe Ile Asn
                165                 170                 175

Thr Phe Gln Arg Gly Pro Gln Glu Ser Val Trp Glu Thr Val Pro Gln
            180                 185                 190

Pro Ser Cys Glu Glu Phe Lys Tyr Gly Gly Lys Asn Gly Tyr Leu Asp
        195                 200                 205

Leu Phe Thr Lys Asp Ala Ser Tyr Ala Lys Gln Trp Lys Tyr Thr Ser
    210                 215                 220

Ala Ser Asp Ala Asp Ala Arg Ala Val Glu Ala Val Tyr Trp Ala Asn
225                 230                 235                 240

Gln Trp Ala Thr Glu Gln Gly Lys Ala Ala Asp Val Ala Ala Thr Val
                245                 250                 255

Ala Lys Ala Ala Lys Met Gly Asp Tyr Leu Arg Tyr Thr Leu Phe Asp
            260                 265                 270

Lys Tyr Phe Lys Lys Ile Gly Cys Thr Ser Pro Thr Cys Ala Ala Gly
        275                 280                 285

Gln Gly Arg Glu Ala Ala His Tyr Leu Leu Ser Trp Tyr Met Ala Trp
    290                 295                 300

Gly Gly Ala Thr Asp Thr Ser Ser Gly Trp Ala Trp Arg Ile Gly Ser
305                 310                 315                 320

Ser His Ala His Phe Gly Tyr Gln Asn Pro Leu Ala Ala Trp Ala Leu
                325                 330                 335

Ser Thr Asp Pro Lys Leu Thr Pro Lys Ser Pro Thr Ala Lys Ala Asp
            340                 345                 350

Trp Ala Ala Ser Met Gln Arg Gln Leu Glu Phe Tyr Thr Trp Leu Gln
        355                 360                 365

Ala Ser Asn Gly Gly Ile Ala Gly Gly Ala Thr Asn Ser Trp Asp Gly
    370                 375                 380

Ala Tyr Ala Gln Pro Pro Ala Gly Thr Pro Thr Phe Tyr Gly Met Gly
385                 390                 395                 400

Tyr Thr Glu Ala Pro Val Tyr Val Asp Pro Pro Ser Asn Arg Trp Phe
                405                 410                 415

Gly Met Gln Ala Trp Gly Val Gln Arg Val Ala Glu Leu Tyr Tyr Ala
            420                 425                 430
```

```
Ser Gly Asn Ala Gln Ala Lys Lys Ile Leu Asp Lys Trp Val Pro Trp
        435                 440                 445

Val Val Ala Asn Ile Ser Thr Asp Gly Ala Ser Trp Lys Val Pro Ser
        450                 455                 460

Glu Leu Lys Trp Thr Gly Lys Pro Asp Thr Trp Asn Ala Ala Ala Pro
465                 470                 475                 480

Thr Gly Asn Pro Gly Leu Thr Val Glu Val Thr Ser Tyr Gly Gln Asp
                485                 490                 495

Val Gly Val Ala Ala Asp Thr Ala Arg Ala Leu Leu Phe Tyr Ala Ala
            500                 505                 510

Lys Ser Gly Asp Thr Ala Ser Arg Asp Lys Ala Lys Ala Leu Leu Asp
            515                 520                 525

Ala Ile Trp Ala Asn Asn Gln Asp Pro Leu Gly Val Ser Ala Val Glu
        530                 535                 540

Thr Arg Gly Asp Tyr Lys Arg Phe Asp Asp Thr Tyr Val Ala Asn Gly
545                 550                 555                 560

Asp Gly Ile Tyr Ile Pro Ser Gly Trp Thr Gly Thr Met Pro Asn Gly
                565                 570                 575

Asp Val Ile Lys Pro Gly Val Ser Phe Leu Asp Ile Arg Ser Phe Tyr
            580                 585                 590

Lys Lys Asp Pro Asn Trp Ser Lys Val Gln Thr Phe Leu Asp Gly Gly
            595                 600                 605

Ala Glu Pro Gln Phe Arg Tyr His Arg Phe Trp Ala Gln Thr Ala Val
        610                 615                 620

Ala Gly Ala Leu Ala Asp Tyr Ala Arg Leu Phe Asp Asp Gly Thr Thr
625                 630                 635                 640

<210> SEQ ID NO 11
<211> LENGTH: 642
<212> TYPE: PRT
<213> ORGANISM: Thermobifida fusca
<220> FEATURE:
<221> NAME/KEY: misc_feature
<223> OTHER INFORMATION: Thermobifida fusca E6

<400> SEQUENCE: 11

Ser Tyr Asp Gln Ala Phe Leu Glu Gln Tyr Glu Lys Ile Lys Asp Pro
1               5                   10                  15

Ala Ser Gly Tyr Phe Arg Glu Phe Asn Gly Leu Leu Val Pro Tyr His
                20                  25                  30

Ser Val Glu Thr Met Ile Val Glu Ala Pro Asp His Gly His Gln Thr
            35                  40                  45

Thr Ser Glu Ala Phe Ser Tyr Tyr Leu Trp Leu Glu Ala Tyr Tyr Gly
        50                  55                  60

Arg Val Thr Gly Asp Trp Lys Pro Leu His Asp Ala Trp Glu Ser Met
65                  70                  75                  80

Glu Thr Phe Ile Ile Pro Gly Thr Lys Asp Gln Pro Thr Asn Ser Ala
                85                  90                  95

Tyr Asn Pro Asn Ser Pro Ala Thr Tyr Ile Pro Glu Gln Pro Asn Ala
            100                 105                 110

Asp Gly Tyr Pro Ser Pro Leu Met Asn Asn Val Pro Val Gly Gln Asp
        115                 120                 125

Pro Leu Ala Gln Glu Leu Ser Ser Thr Tyr Gly Thr Asn Glu Ile Tyr
    130                 135                 140

Gly Met His Trp Leu Leu Asp Val Asp Asn Val Tyr Gly Phe Gly Phe
145                 150                 155                 160
```

-continued

```
Cys Gly Asp Gly Thr Asp Asp Ala Pro Ala Tyr Ile Asn Thr Tyr Gln
                165                 170                 175
Arg Gly Ala Arg Glu Ser Val Trp Glu Thr Ile Pro His Pro Ser Cys
            180                 185                 190
Asp Asp Phe Thr His Gly Gly Pro Asn Gly Tyr Leu Asp Leu Phe Thr
        195                 200                 205
Asp Asp Gln Asn Tyr Ala Lys Gln Trp Arg Tyr Thr Asn Ala Pro Asp
    210                 215                 220
Ala Asp Ala Arg Ala Val Gln Val Met Phe Trp Ala His Glu Trp Ala
225                 230                 235                 240
Lys Glu Gln Gly Lys Glu Asn Glu Ile Ala Gly Leu Met Asp Lys Ala
                245                 250                 255
Ser Lys Met Gly Asp Tyr Leu Arg Tyr Ala Met Phe Asp Lys Tyr Phe
            260                 265                 270
Lys Lys Ile Gly Asn Cys Val Gly Ala Thr Ser Cys Pro Gly Gly Gln
        275                 280                 285
Gly Lys Asp Ser Ala His Tyr Leu Leu Ser Trp Tyr Tyr Ser Trp Gly
    290                 295                 300
Gly Ser Leu Asp Thr Ser Ser Ala Trp Ala Trp Arg Ile Gly Ser Ser
305                 310                 315                 320
Ser Ser His Gln Gly Tyr Gln Asn Val Leu Ala Ala Tyr Ala Leu Ser
                325                 330                 335
Gln Val Pro Glu Leu Gln Pro Asp Ser Pro Thr Gly Val Gln Asp Trp
            340                 345                 350
Ala Thr Ser Phe Asp Arg Gln Leu Glu Phe Leu Gln Trp Leu Gln Ser
        355                 360                 365
Ala Glu Gly Gly Ile Ala Gly Ala Thr Asn Ser Trp Lys Gly Ser
    370                 375                 380
Tyr Asp Thr Pro Pro Thr Gly Leu Ser Gln Phe Tyr Gly Met Tyr Tyr
385                 390                 395                 400
Asp Trp Gln Pro Val Trp Asn Asp Pro Ser Asn Trp Phe Gly
                405                 410                 415
Phe Gln Val Trp Asn Met Glu Arg Val Ala Gln Leu Tyr Tyr Val Thr
            420                 425                 430
Gly Asp Ala Arg Ala Glu Ala Ile Leu Asp Lys Trp Val Pro Trp Ala
        435                 440                 445
Ile Gln His Thr Asp Val Asp Ala Asp Asn Gly Gly Gln Asn Phe Gln
    450                 455                 460
Val Pro Ser Asp Leu Glu Trp Ser Gly Gln Pro Asp Thr Trp Thr Gly
465                 470                 475                 480
Thr Tyr Thr Gly Asn Pro Asn Leu His Val Gln Val Val Ser Tyr Ser
                485                 490                 495
Gln Asp Val Gly Val Thr Ala Ala Leu Ala Lys Thr Leu Met Tyr Tyr
            500                 505                 510
Ala Lys Arg Ser Gly Asp Thr Thr Ala Leu Ala Thr Ala Glu Gly Leu
        515                 520                 525
Leu Asp Ala Leu Leu Ala His Arg Asp Ser Ile Gly Ile Ala Thr Pro
    530                 535                 540
Glu Gln Pro Ser Trp Asp Arg Leu Asp Asp Pro Trp Asp Gly Ser Glu
545                 550                 555                 560
Gly Leu Tyr Val Pro Pro Gly Trp Ser Gly Thr Met Pro Asn Gly Asp
                565                 570                 575
```

-continued

```
Arg Ile Glu Pro Gly Ala Thr Phe Leu Ser Ile Arg Ser Phe Tyr Lys
            580                 585                 590

Asn Asp Pro Leu Trp Pro Gln Val Glu Ala His Leu Asn Asp Pro Gln
        595                 600                 605

Asn Val Pro Ala Pro Ile Val Glu Arg His Arg Phe Trp Ala Gln Val
    610                 615                 620

Glu Ile Ala Thr Ala Phe Ala Ala His Asp Glu Leu Phe Gly Ala Gly
625                 630                 635                 640

Ala Pro
```